United States Patent
Edwards et al.

(10) Patent No.: US 11,278,454 B2
(45) Date of Patent: Mar. 22, 2022

(54) METHODS OF MANAGING MOISTURE WHEN USING A LOW PROFILE WOUND CONNECTION CONDUIT

(71) Applicant: KCI Licensing, Inc., San Antonio, TX (US)

(72) Inventors: Thomas Alan Edwards, Southampton (GB); Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 180 days.

(21) Appl. No.: 16/529,615

(22) Filed: Aug. 1, 2019

(65) Prior Publication Data

US 2020/0060879 A1  Feb. 27, 2020

Related U.S. Application Data

(60) Provisional application No. 62/722,321, filed on Aug. 24, 2018.

(51) Int. Cl.
*A61F 13/02* (2006.01)
*A61M 1/00* (2006.01)
*A61F 13/00* (2006.01)

(52) U.S. Cl.
CPC ........... *A61F 13/0216* (2013.01); *A61M 1/85* (2021.05); *A61M 1/962* (2021.05);
(Continued)

(58) Field of Classification Search
CPC ...... A61F 13/0216; A61F 2013/00174; A61M 1/85; A61M 1/73; A61M 1/74; A61M 2205/3344
See application file for complete search history.

(56) References Cited

U.S. PATENT DOCUMENTS 1,355,846 A  10/1920  Rannells
2,547,758 A   4/1951  Keeling
(Continued)

FOREIGN PATENT DOCUMENTS

AU  550575 B2  3/1986
AU  745271 B2  3/2002
(Continued)

OTHER PUBLICATIONS

International Search Report and Written Opinion for Corresponding Application No. PCT/US2019/044704, dated Oct. 31, 2019.
(Continued)

*Primary Examiner* — Susan S Su
*Assistant Examiner* — Eric Rassavong

(57) ABSTRACT

A low-profile dressing interface or connector may comprise at least two side-by-side fluid pathways fluidly coupled to a recessed space of the connector, one for providing negative pressure to a tissue interface and the other for sensing negative pressure within the recessed space adjacent the tissue interface. The apparatus may comprise a top layer having a plurality of closed cells with tapered sidewalls. The apparatus may also comprise a base layer forming a sealed space between the top layer and the base layer. The base layer may further include a plurality of closed cells having tapered sidewalls. The apparatus may then further comprise a barrier coupled between the top layer and the base layer to form two fluid pathways within the sealed space.

38 Claims, 23 Drawing Sheets

(52) U.S. Cl.
CPC ...... *A61F 2013/00174* (2013.01); *A61M 1/73* (2021.05); *A61M 1/74* (2021.05); *A61M 2205/3344* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,294,387 A | 12/1966 | Chavannes | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 10,548,777 B2 * | 2/2020 | Locke | A61F 13/00068 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0036334 A1 | 2/2010 | Heagle et al. | |
| 2014/0163491 A1 | 6/2014 | Schuessler et al. | |
| 2014/0316358 A1 * | 10/2014 | Coulthard | A61M 1/784 604/319 |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2815731 A1 | 12/2014 |
| EP | 2815731 A1 * 12/2014 | ....... A61F 13/00068 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |

(56) References Cited

FOREIGN PATENT DOCUMENTS

| JP | 4129536 B2 | 8/2008 | | |
|---|---|---|---|---|
| SG | 71559 | 4/2002 | | |
| WO | 80/02182 A1 | 10/1980 | | |
| WO | 87/04626 A1 | 8/1987 | | |
| WO | 90/010424 A1 | 9/1990 | | |
| WO | 93/009727 A1 | 5/1993 | | |
| WO | 94/20041 A1 | 9/1994 | | |
| WO | 96/05873 A1 | 2/1996 | | |
| WO | 97/18007 A1 | 5/1997 | | |
| WO | 99/13793 A1 | 3/1999 | | |
| WO | 2017119996 A1 | 7/2017 | | |
| WO | WO-2017119996 A1 * | 7/2017 | .......... | A61M 1/0031 |
| WO | 2019084006 A1 | 5/2019 | | |

OTHER PUBLICATIONS

Louis C. Argenta, Md and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, Md et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634 639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C. ® Therapy Clinical Guidelines: A Reference Source for Clinicians; Jul. 2007.

* cited by examiner

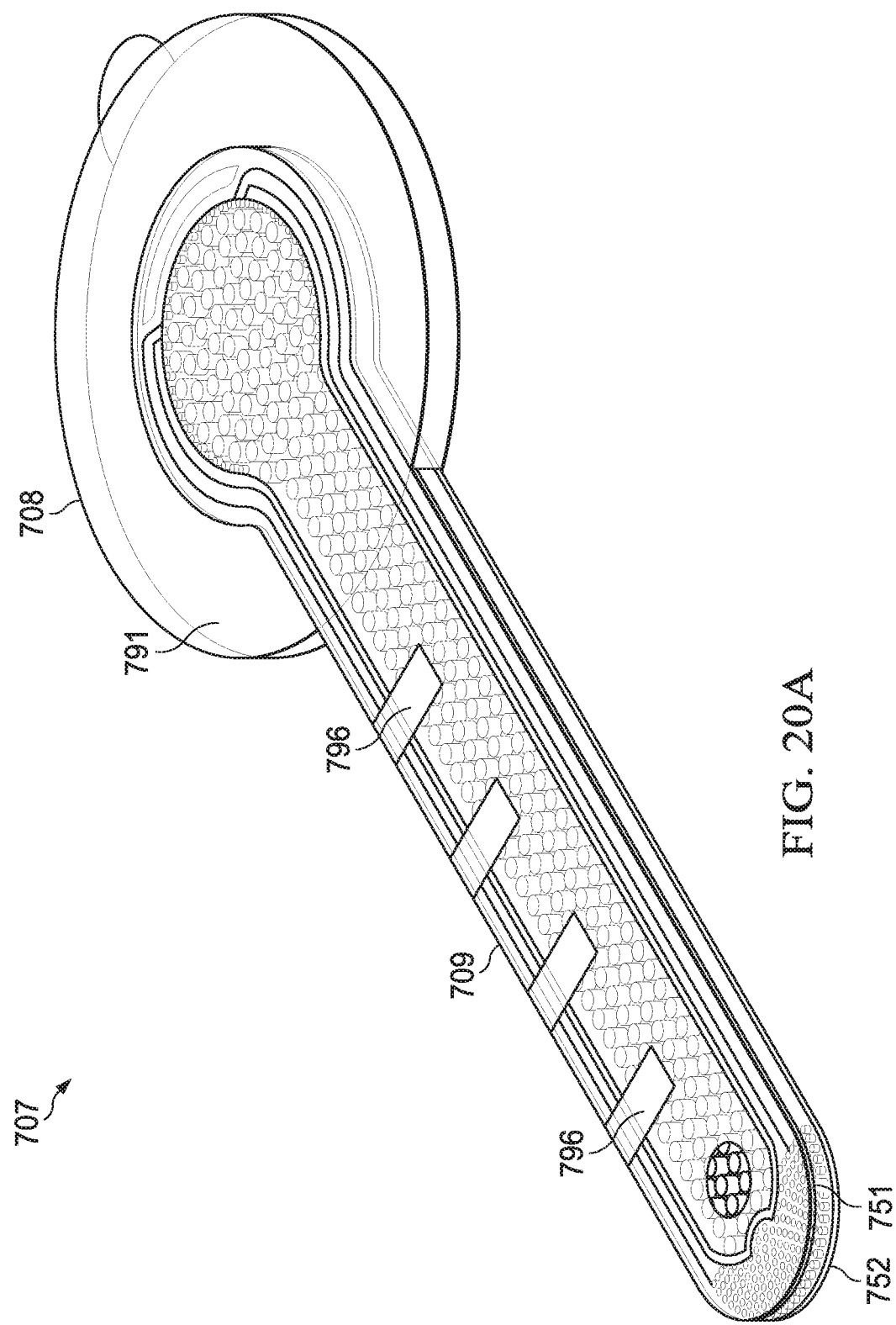

METHODS OF MANAGING MOISTURE WHEN USING A LOW PROFILE WOUND CONNECTION CONDUIT

RELATED APPLICATIONS

The present application claims the benefit, under 35 USC § 119(e), of the filing of U.S. Provisional Patent Application Ser. No. 62/722,321, entitled "Methods of Managing Moisture When Using a Low Profile Wound Connection Conduit," filed Aug. 24, 2018, which is incorporated herein by reference for all purposes.

TECHNICAL FIELD

The invention set forth in the appended claims relates generally to tissue treatment systems and more particularly, but without limitation, to apparatuses and methods for providing negative-pressure therapy using low profile distribution components for wound therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for instilling fluid to a tissue site in a negative-pressure therapy environment are set forth in the appended claims. Illustrative embodiments are also provided to enable a person skilled in the art to make and use the claimed subject matter. Some embodiments are illustrative of an apparatus or system for delivering negative-pressure to a tissue site, which can be used in conjunction with low profile distribution components for wound therapy. For example, an apparatus may include a low profile dressing interface comprising at least two side-by-side fluid pathways fluidly coupled to a recessed space of the connector, one for providing negative pressure to a tissue interface or manifold and the other for sensing the negative pressure within the recessed space adjacent the tissue interface.

In some embodiments, for example, an apparatus for managing fluid in a system for treating a tissue site may comprise a first layer including polymeric film and a second layer including polymeric film coupled to the first layer to form a sealed space between the first layer and the second layer. In some embodiments, the sealed space may include a port at a proximal end of the sealed space. The apparatus may further comprise a first inner layer including a polymeric film disposed between the first layer and the second layer such that the first inner layer defines a plurality of closed cells with the first layer. The closed cells may include sidewalls having a thickness tapering from the first layer to a distal end within the sealed space. The apparatus may further comprise an applicator having an aperture formed in the second layer at the distal end of the sealed space, wherein the aperture exposes a portion of the plurality of closed cells to define a recessed space adapted to be fluidly coupled to the tissue site.

In some embodiments, the apparatus may further comprise a barrier coupled between the first layer and the second layer to form two fluid pathways within the sealed space that extends between the recessed space and the port. In some embodiments, the apparatus may further comprise a second inner layer including a polymeric film disposed between the first layer and the second layer and defining a plurality of closed cells with the second layer. The closed cells may include sidewalls having a thickness tapering from the second layer to a distal end within the sealed space.

In some embodiments, the polymeric film may be, for example, a polyurethane film having an average thickness between about 250 μm and about 1000 μm. In some example embodiments, the polymeric film may be polyurethane having an average thickness between about 250 μm and about 1000 μm and the distal end of the closed cells may have an average thickness between about 50 μm and about 250 μm. In yet another example embodiment, the polymeric film may be polyurethane and the distal ends of the closed cells may have a thickness of less than about 40% of a thickness of either the first or second layer.

In some embodiments, for example, an apparatus for managing fluid in a system for treating a tissue site may comprise a top layer including polymeric film having a plurality of closed cells including sidewalls tapering from the top layer to a distal end of the closed cells. The apparatus may further comprise a base layer including polymeric film coupled to the top layer with a seal forming a sealed space between the top layer and the base layer, the sealed space including port at the proximal end of the sealed space. The apparatus also may comprise an applicator having an aperture formed in the base layer at the distal end of the sealed space, wherein the aperture exposes a portion of the plurality of closed cells to define a recessed space adapted to be fluidly coupled to the tissue site. In some embodiments, the apparatus may further comprise a first barrier coupled between the top layer and the base layer to form two fluid pathways within the sealed space between the recessed space and the port. In some embodiments, the port may comprise an outlet adapted to be fluidly coupled to a source of negative pressure and a first inlet adapted to be fluidly coupled to a pressure sensor. In yet other example embodiments, the apparatus may further comprise a second barrier coupled between the top layer and the base layer to form a total of three fluid pathways within the sealed space between the recessed space and the port.

In some embodiments, for example, another apparatus for managing fluid in a system for treating a tissue site may comprise a top layer including polymeric film having a plurality of closed cells including sidewalls tapering from the top layer to a distal end of the closed cells. The apparatus may further comprise a base layer including polymeric film coupled to the top layer with a seal forming a sealed space between the top layer and the base layer. The base layer may further include a plurality of closed cells having sidewalls tapering from the base layer to a distal end of the closed cells. The apparatus may further comprise an applicator having an aperture formed in the base layer at the distal end of the sealed space and exposing a portion of the plurality of closed cells. The apparatus may also comprise a barrier coupled between the top layer and the base layer to form two fluid pathways within the sealed space. In some embodiments, the distal ends of the closed cells extending from the top layer may be arranged to contact the distal ends of the closed cells extending from the base layer.

A method for providing negative pressure to a sealed space in fluid communication with a tissue site is also disclosed. In one example embodiment, the method comprises positioning a tissue interface or manifold at a tissue site for delivering negative pressure to the tissue site, and coupling a recessed space of a dressing interface or a connector to the tissue interface or manifold wherein the dressing interface comprises a first fluid pathway and a second fluid pathway that are fluidly coupled to the recessed space in a side-by-side relationship. Such method further comprises applying negative pressure to the recessed space through the first fluid pathway formed by a first layer of polymeric film coupled to a second layer of polymeric film including features separating the first layer and the second layer to form the first pathway. Such method further comprises sensing the negative pressure within the recessed space through the second fluid pathway formed by the first layer and the second layer including features separating the first layer and the second layer to form the second pathway. The features or closed cells within the first pathway and the second pathway may prevent the pathways from collapsing as a result of apposition forces generated by the application of negative pressure to the dressing interface or connector. These features or closed cells may also prevent the negative pressure or pressure sensing from being blocked as a result of external forces being applied to the dressing interface or connector.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIGS. 20A and 20B is a perspective view of the top and bottom of the third dressing interface shown in FIG. 10 including a moisture offloading layer and moisture evaporation tabs that may be associated with some example embodiments of the third dressing interface.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

Figure 1:
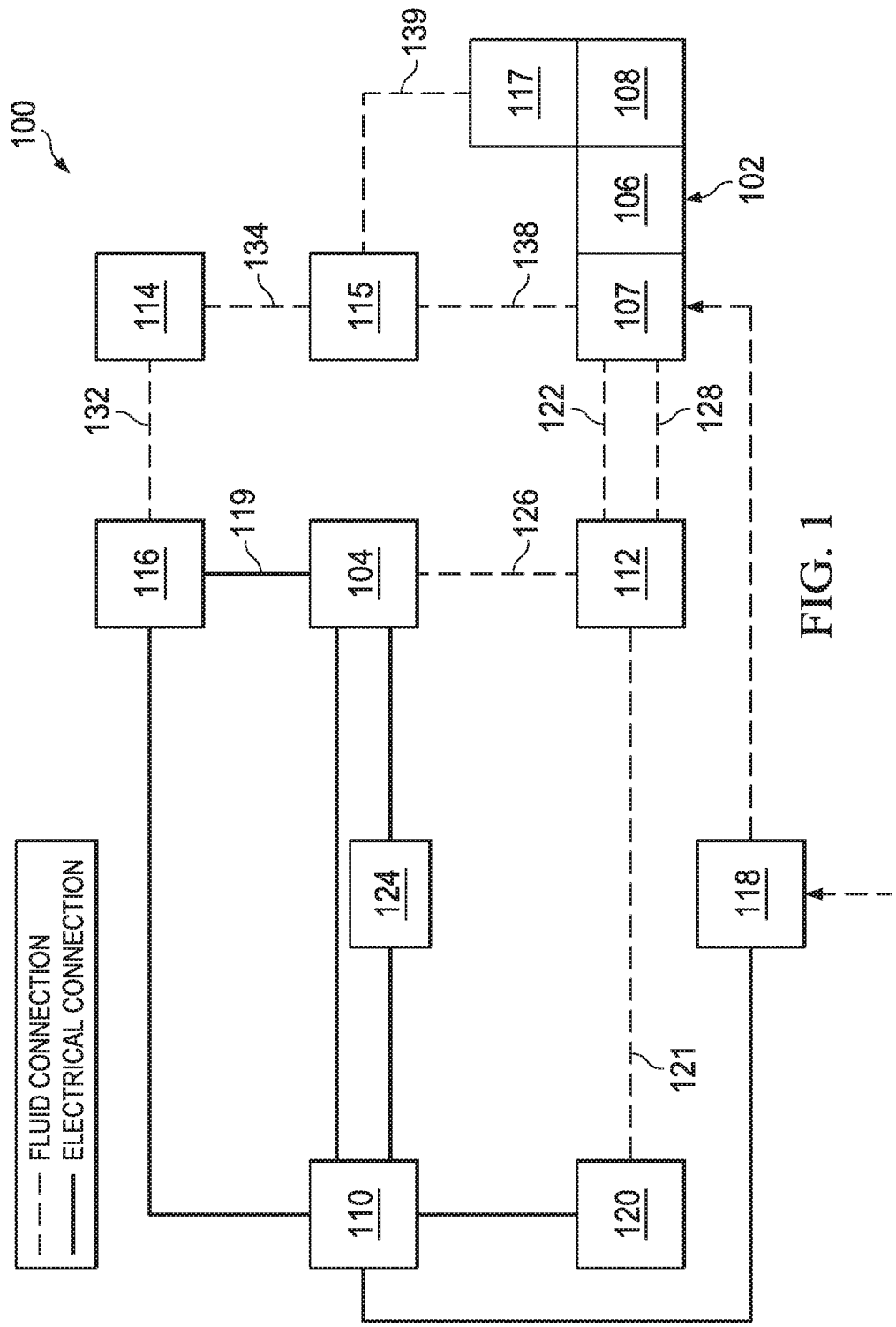
FIG. 1 is a functional block diagram of an example embodiment of a therapy system that can provide negative-pressure and instillation in accordance with this specification.
Figure 2:
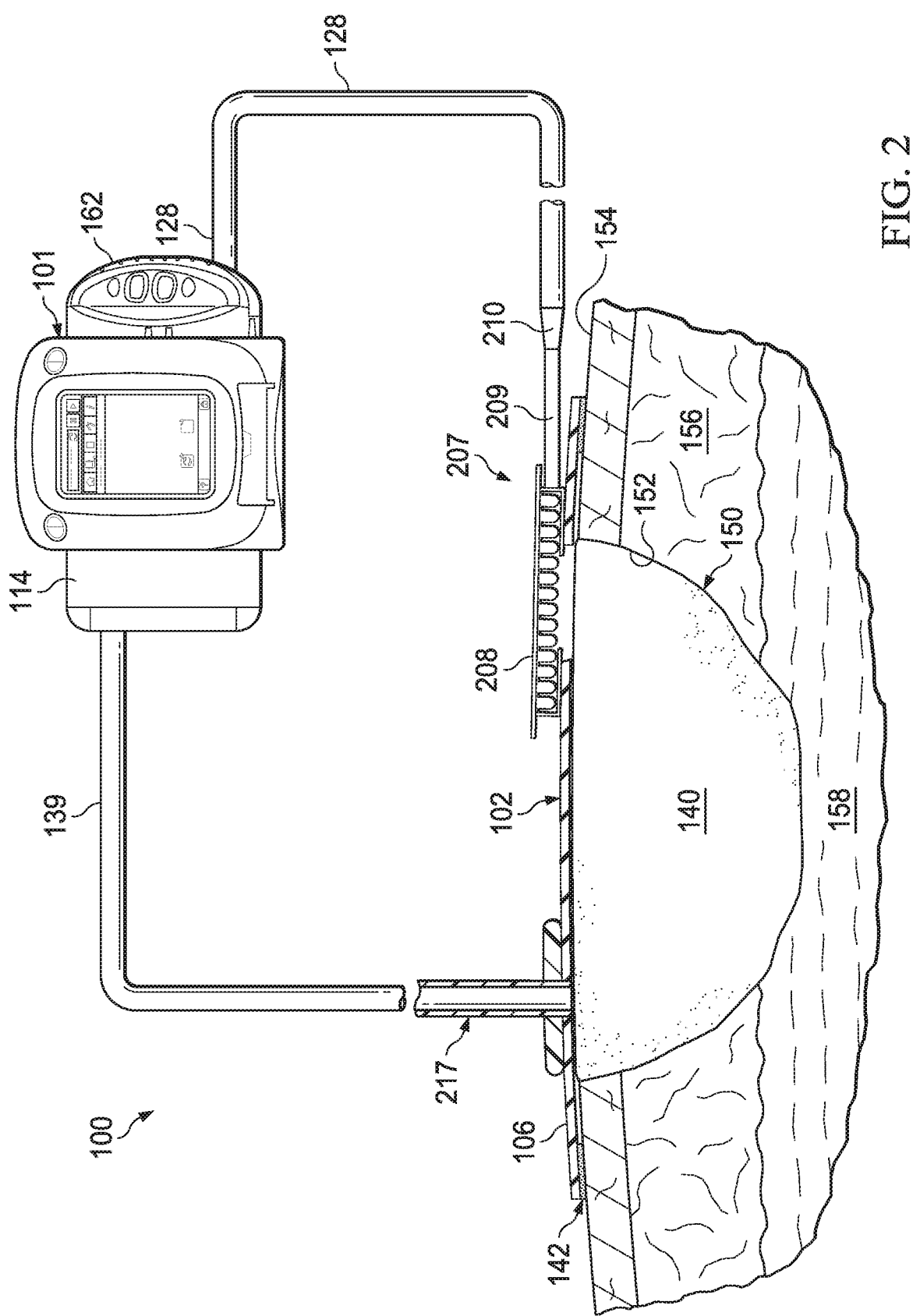
FIG. 2 is a schematic diagram of an example embodiment of the negative-pressure and instillation therapy system of FIG. 1 for delivering negative pressure and treatment solutions to a dressing at a tissue site.

The present technology also provides negative pressure therapy devices and systems, and methods of treatment using such systems with antimicrobial solutions. FIG. 1 is a simplified functional block diagram of an example embodiment of a therapy system 100 that can provide negative-pressure therapy with instillation of treatment solutions in accordance with this specification. FIG. 2 is a schematic diagram of an example embodiment of the negative-pressure and instillation therapy system of FIG. 1 for delivering negative pressure and treatment solutions to a dressing at a tissue site. The therapy system 100 may be packaged as a single, integrated unit such as therapy system 101. The therapy system 101 may be, for example, a V.A.C. Ulta™ System available from Kinetic Concepts, Inc. of San Antonio, Tex.

The therapy system 100 may include a negative-pressure supply, and may include or be configured to be coupled to a distribution component, such as a dressing. In general, a distribution component may refer to any complementary or ancillary component configured to be fluidly coupled to a negative-pressure supply between a negative-pressure supply and a tissue site. A distribution component is preferably detachable, and may be disposable, reusable, or recyclable. For example, a dressing 102 is illustrative of a distribution component fluidly coupled to a negative-pressure source 104 in FIG. 1. A dressing may include a cover, a tissue interface, or both in some embodiments. The dressing 102, for example, may include a cover 106, a dressing interface 107, and a tissue interface 108. A computer or a controller device, such as a controller 110, may also be coupled to the negative-pressure source 104. In some embodiments, the cover 106 may be configured to cover the tissue interface 108 and the tissue site, and may be adapted to seal the tissue interface and create a therapeutic environment proximate to a tissue site for maintaining a negative pressure at the tissue site. In some embodiments, the dressing interface 107 may be configured to fluidly couple the negative-pressure source 104 to the therapeutic environment of the dressing. The therapy system 100 may optionally include a fluid container, such as a container 112, coupled to the dressing 102 and to the negative-pressure source 104.

The therapy system 100 may also include a source of instillation solution, such as a solution source 114. A distribution component may be fluidly coupled to a fluid path between a solution source and a tissue site in some embodiments. For example, an instillation pump 116 may be coupled to the solution source 114, as illustrated in the example embodiment of FIG. 1. The instillation pump 116 may also be fluidly coupled to the negative-pressure source 104 such as, for example, by a fluid conductor 119. In some embodiments, the instillation pump 116 may be directly coupled to the negative-pressure source 104, as illustrated in FIG. 1, but may be indirectly coupled to the negative-pressure source 104 through other distribution components in some embodiments. For example, in some embodiments, the instillation pump 116 may be fluidly coupled to the negative-pressure source 104 through the dressing 102. In some embodiments, the instillation pump 116 and the negative-pressure source 104 may be fluidly coupled to two different locations on the same tissue interface 108 by two different dressing interfaces. For example, the negative-pressure source 104 may be fluidly coupled to the dressing interface 107 at a first location, while the installation pump 116 may be fluidly to the coupled to dressing interface 117 at a second location, e.g., dressing interface 207 and dressing interface 217 as shown in FIG. 2.

The therapy system 100 also may include sensors to measure operating parameters and provide feedback signals to the controller 110 indicative of the operating parameters. As illustrated in FIG. 1, for example, the therapy system 100 may include a pressure sensor 120 for measuring wound pressure and/or sensor 124 for measuring other properties in the therapy system 100 such as, for example, various pressures, voltages and currents. The pressure sensor 120 and the sensor 124 may be electrically coupled to the controller 110 for providing information to the therapy system 100. The pressure sensor 120 may be fluidly coupled or configured to be fluidly coupled to a distribution component such as, for example, the negative-pressure source 104 either directly or indirectly through the container 112. The pressure sensor 120 may be configured to measure pressure being generated by the negative-pressure source 104, i.e., the pump pressure (PP). The sensor 124 may be a sensor that is coupled to the negative-pressure source 104 to measure the pump pressure (PP). In some example embodiments, the sensor 124 may be a sensor in fluid communication with the output of the negative-pressure source 104 to directly measure the pump pressure (PP). In other example embodiments, the sensor 124 may be a sensor electrically coupled to the negative-pressure source 104 to measure the changes in the current in order to determine the pump pressure (PP).

Distribution components may be fluidly coupled to each other to provide a distribution system for transferring fluids (i.e., liquid and/or gas). For example, a distribution system may include various combinations of fluid conductors and fittings to facilitate fluid coupling. A fluid conductor generally includes any structure with one or more lumina adapted to convey a fluid between two ends, such as a tube, pipe, hose, or conduit. Typically, a fluid conductor is an elongated, cylindrical structure with some flexibility, but the geometry and rigidity may vary. Some fluid conductors may be molded into or otherwise integrally combined with other components. A fitting can be used to mechanically and fluidly couple components to each other. For example, a fitting may comprise a projection and an aperture. The projection may be configured to be inserted into a fluid conductor so that the aperture aligns with a lumen of the fluid conductor. A valve is a type of fitting that can be used to control fluid flow. For example, a check valve can be used to substantially prevent return flow. A port is another example of a fitting. A port may also have a projection, which may be threaded, flared, tapered, barbed, or otherwise configured to provide a fluid seal when coupled to a component.

In some embodiments, distribution components may also be coupled by virtue of physical proximity, being integral to a single structure, or being formed from the same piece of material. Coupling may also include mechanical, thermal, electrical, or chemical coupling (such as a chemical bond) in some contexts. For example, a tube may mechanically and fluidly couple the dressing 102 to the container 112 in some embodiments. In general, components of the therapy system 100 may be coupled directly or indirectly. For example, the negative-pressure source 104 may be directly coupled to the controller 110, and may be indirectly coupled to the dressing interface 107 through the container 112 by conduit 126 and conduit 128. The pressure sensor 120 may be fluidly coupled to the dressing 102 directly or indirectly by conduit 121 and conduit 122. Additionally, the installation pump 116 may be coupled indirectly to the dressing interface 107 through the solution source 114 and the installation regulator 115 by fluid conductors 132, 134 and 138. Alternatively, the installation pump 116 may be coupled indirectly to the second dressing interface 117 through the solution source 114 and the installation regulator 115 by fluid conductors 132, 134 and 139.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold 140. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam manifold may vary according to needs of a prescribed therapy. For example, in some embodiments, the tissue interface 108 may be a foam manifold having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or Vera-Flo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device, such as an attachment device 142, may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, a dressing interface may facilitate coupling the negative-pressure source 104 to the dressing 102. The negative pressure provided by the negative-pressure source 104 may be delivered through the conduit 128 to a negative-pressure connector that in some embodiments may include an elbow connector (not shown) having a first end adapted to be positioned in fluid communication with the manifold 140 and a second end extending at a substantially right angle from the first end adapted to be fluidly coupled to the conduit 128. In some embodiments, the elbow connector may be substantially rigid. In yet another example embodiment, the negative-pressure interface may be semi-rigid such as, for example, a T.R.A.C.® Pad or Sensa T.R.A.C.® Pad available from KCI of San Antonio, Tex. The negative-pressure interface delivers negative pressure within an interior portion of the cover 106 and the manifold 140.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to control one or more operating parameters of the therapy system 100. Operating parameters may include, for example, the power applied to the negative-pressure source 104, the pressure generated by the negative-pressure source 104, or the pressure distributed to the tissue interface 108. The controller 110 is also preferably configured to receive one or more input signals and programmed to modify one or more operating parameters based on the input signals.

Sensors, such as the pressure sensor 120 or the sensor 124, are generally known in the art as any apparatus operable to detect or measure a physical phenomenon or property, and generally provide a signal indicative of the phenomenon or property that is detected or measured. For example, the pressure sensor 120 and the sensor 124 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The sensor 124 may optionally be a sensor to measure operating parameters of the negative-pressure source 104, such as the voltage or current, in some embodiments. Preferably, the signals from the pressure sensor 120 and the sensor 124 are suitable as an input signal to the controller 110, but some signal conditioning may be appropriate in some embodiments. For example, the signal may need to be filtered or amplified before it can be processed by the controller 110. Typically, the signal is an electrical signal that is transmitted and/or received on by wire or wireless means, but may be represented in other forms, such as an optical signal.

The solution source 114 is representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions. Examples of such other therapeutic solutions that may be suitable for some prescriptions include hypochlorite-based solutions, silver nitrate (0.5%), sulfur-based solutions, biguanides, cationic solutions, and isotonic solutions. In one illustrative embodiment, the solution source 114 may include a storage component for the solution and a separate cassette for holding the storage component and delivering the solution to the tissue site 150, such as a V.A.C. VeraLink™ Cassette available from Kinetic Concepts, Inc. of San Antonio, Tex.

The container 112 may also be representative of a container, canister, pouch, or other storage component, which can be used to collect and manage exudates and other fluids withdrawn from a tissue site. In many environments, a rigid container such as, for example, a container 162, may be preferred or required for collecting, storing, and disposing of fluids. In other environments, fluids may be properly disposed of without rigid container storage, and a re-usable container could reduce waste and costs associated with negative-pressure therapy. In some embodiments, the container 112 may comprise a canister having a collection chamber, a first inlet fluidly coupled to the collection chamber and a first outlet fluidly coupled to the collection chamber and adapted to receive negative pressure from a source of negative pressure. In some embodiments, a first fluid conductor may comprise a first member such as, for example, the conduit 128 fluidly coupled between the first inlet and the tissue interface 108 by the negative-pressure interface, and a second member such as, for example, the conduit 126 fluidly coupled between the first outlet and a source of negative pressure whereby the first conductor is adapted to provide negative pressure within the collection chamber to the tissue site.

The therapy system 100 may also comprise a flow regulator such as, for example, a regulator 118 fluidly coupled to a source of ambient air to provide a controlled or managed flow of ambient air to the sealed therapeutic environment provided by the dressing 102 and ultimately the tissue site. In some embodiments, the regulator 118 may control the flow of ambient fluid to purge fluids and exudates from the sealed therapeutic environment. In some embodiments, the regulator 118 may be fluidly coupled to the tissue interface 108 through the dressing interface 107. The regulator 118 may be configured to fluidly couple the tissue interface 108 to a source of ambient air as indicated by a dashed arrow. In some embodiments, the regulator 118 may be disposed within the therapy system 100 rather than being proximate to the dressing 102 so that the air flowing through the regulator 118 is less susceptible to accidental blockage during use. In such embodiments, the regulator 118 may be positioned proximate the container 112 and/or proximate a source of ambient air where the regulator 118 is less likely to be blocked during usage.

In operation, the tissue interface 108 may be placed within, over, on, or otherwise proximate a tissue site, such as tissue site 150. The cover 106 may be placed over the tissue interface 108 and sealed to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

As discussed above, the tissue site 150 may include, without limitation, any irregularity with a tissue, such as an open wound, surgical incision, or diseased tissue. The therapy system 100 is presented in the context of a tissue site that includes a wound 152, which is through the epidermis 154, or generally skin, and the dermis 156 and reaching into a hypodermis, or subcutaneous tissue 158. The therapy system 100 may be used to treat a wound of any depth, as well as many different types of wounds including open wounds, incisions, or other tissue sites. The tissue site 150 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 150 may include removal of fluids originating from the tissue site 150, such as exudates or ascites, or fluids instilled into the dressing to cleanse or treat the tissue site 150, such as antimicrobial solutions.

When applying negative pressure to the tissue site 150, the dressing interface 107 may include an elbow connector (not shown) as the negative-pressure interface which may be fluidly coupled to the conduit 128 for delivering the negative pressure to the tissue site 150 as described above. In some embodiments, a rigid elbow connector may be utilized so that it does not collapse when delivering the negative pressure and less likely to become included. However, a rigid elbow connector may be uncomfortable for a patient if the patient accidentally rolls over on the connector or if the tissue site 150 is located underneath the patient. What is needed is a low profile, flexible dressing interface that collapsing from external forces so that the negative pressure continues to be provided to the tissue site and measured by the pressure sensor without interrupting the intended therapy for the patient or making the patient uncomfortable. The systems, apparatuses, and methods described herein include improvements that overcome the disadvantages associated with a rigid elbow connector and provide other significant advantages as described below. For example, the negative pressure interface may include a dressing interface 207 substantially similar to the dressing interface 107 described above that is substantially flat and flexible, but also compressible without including or blocking the fluid pathway between the conduit 128 and the manifold 140. In some embodiments, the dressing interface 207 comprises an applicator 208 adapted to be positioned in fluid communication with the manifold 140 and a bridge 209 fluidly coupled to the applicator 208 and extending to an adapter 210. The adapter 210 may be configured to fluidly couple the substantially flat bridge 209 to the conduit 128 that is tubular in shape.

Figure 3:
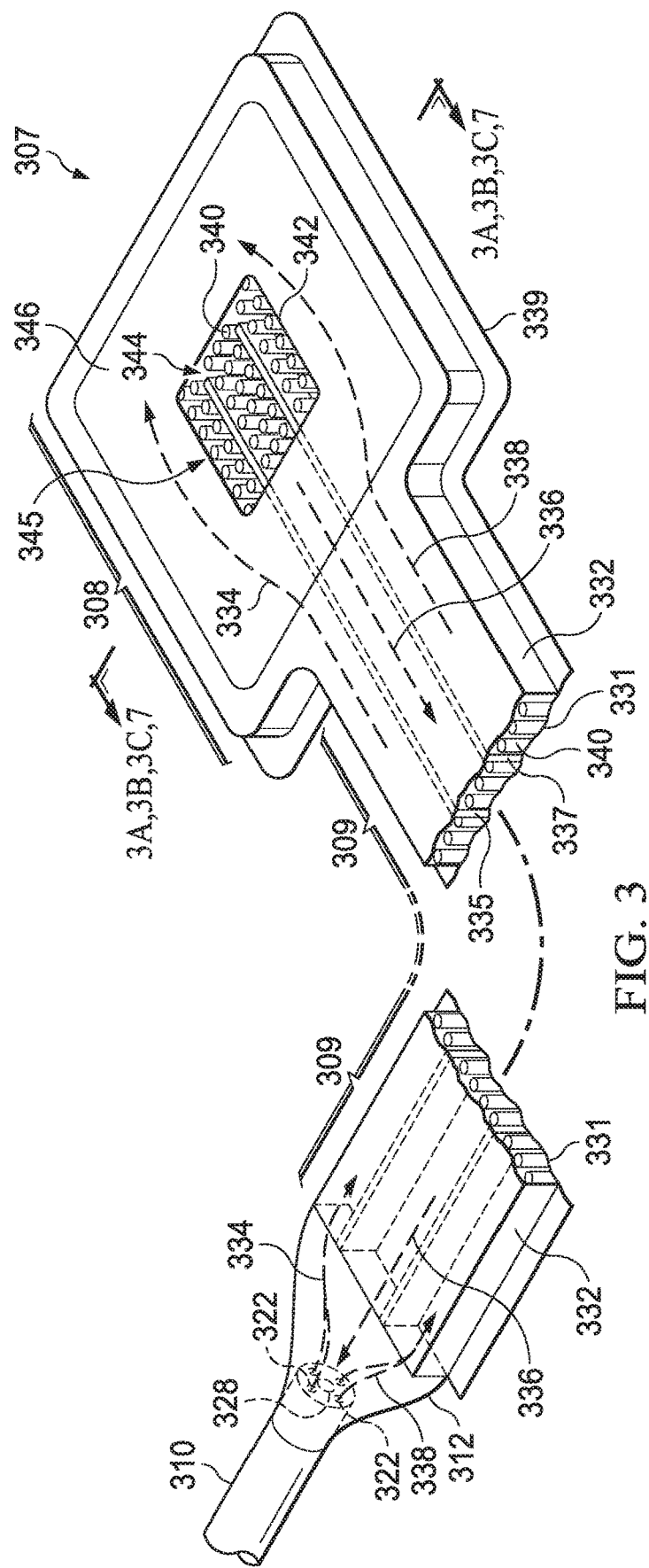
FIG. 3 is a segmented perspective bottom view of a first dressing interface having a low profile structure that may be associated with some example embodiments of the therapy system of FIG. 1.
Figure 3A:
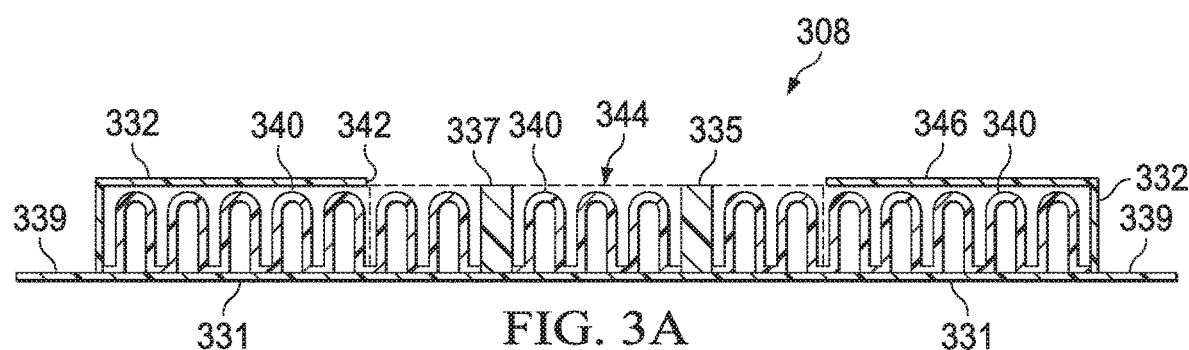
FIGS. 3A, 3B and 3C are cross-sectional views taken along lines 3A-3A, 3B-3B, and 3C-3C in FIG. 3 of three embodiments of the first dressing interface showing a first and second layer of the first dressing interface including different configurations of closed cells associated with the first and/or second layers.

Referring now to FIG. 3, a segmented perspective bottom view of a dressing interface 307 having a low profile structure that may be associated with some example embodiments of the therapy systems of FIGS. 1 and 3 is shown, with further reference to FIG. 3A that is a cross-sectional view taken along line 3A-3A in FIG. 3. Functionally, the dressing interface 307 is substantially similar to the dressing interface 107 as described above. The dressing interface 307 may comprise an applicator 308 and a bridge 309 fluidly coupled to the applicator 308. The applicator 308 may be bulbous or any shape suitable for applying therapy to the manifold 140 and depending on the size and nature of the tissue site 150. The bridge 309 of the dressing interface 307 may be long and narrow and adapted to be fluidly coupled to a tube or conduit 310 by an adapter 312 for delivering and sensing negative pressure. In one example embodiment, the conduit 310 may comprise the conduit 128 for delivering negative pressure to the dressing interface 307 and the conduit 122 for sensing negative pressure at the tissue interface 108. For example, the conduit 310 may comprise a central lumen 328 for delivering negative pressure to the dressing interface 307 and peripheral lumens 322 for sensing negative pressure at the tissue interface 108. The other end of the conduit 310 may be fluidly coupled to the negative-pressure source 104 and the pressure sensor 120 either directly or indirectly through the canister 112 as described above in more detail.

In some example embodiments, the applicator 308 and the bridge 309 of the dressing interface 307 may comprise a top layer such as, for example, a first layer 331, and a base layer such as, for example, a second layer 332, coupled to the first layer 331 around the periphery of the first layer 331 to form a sealed space within the dressing interface 307. Thus, the sealed space may be formed between the first layer 331 and the second layer 332 of both the applicator 308 and the bridge 309 of the dressing interface 307. The first layer 331 and the second layer 332 may both be formed from or include a polymeric film. The first layer 331 and the second layer 332 may be coupled around the periphery of the dressing interface 307 to form the sealed space by welding (RF or ultrasonic), heat sealing, or adhesive bonding such as, for example, acrylics or cured adhesives. For example, the first layer 331 and the second layer 332 may be welded together around the periphery of the dressing interface 307, and may form a flange 339 around the periphery of the dressing interface 307 as a result of the weld. One skilled in the art would understand that there are a variety of methods for coupling the first layer 331 and the second layer 332 to form the sealed space within the dressing interface 307.

The dressing interface 307 may further comprise at least one barrier or wall such as, for example, a first wall 335, coupled between the first layer 331 and the second layer 332. In some embodiments, the first wall 335 may extend from the end of the bridge 309 adjacent the adapter 312 into the applicator 308 to form at least two sealed spaces or fluid pathways between the first layer 331 and the second layer 332 within the dressing interface 307. In another example embodiment, the dressing interface 307 may further comprise a second barrier such as, for example, a second wall 337, coupled between the first layer 331 and the second layer 332. In some embodiments, the second wall 337 also may extend from the end of the bridge 309 adjacent the adapter 312 into the applicator 308. In some example embodiments, the wall 335 and the wall 337 may comprise a polymeric film coupled between the first layer 331 and the second layer 332. In some other example embodiments, the wall 335 and the wall 337 may comprise a weld (RF or ultrasonic), a heat seal, an adhesive bond, or a combination of any of the foregoing. In those embodiments comprising two walls, e.g., the first wall 335 and the second wall 337, such embodiments may form three sealed spaces or fluid pathways within the sealed space between the first layer 331 and the second layer 332. In some embodiments, two of the fluid pathways may be dedicated to measuring pressure such as, for example, pressure sensing pathways 334 and 338 (as indicated by the dashed line arrows), leaving one of the fluid pathways to be utilized for providing negative pressure such as, for example, negative pressure pathway 336 (as indicated by the dashed line arrows).

In some example embodiments, the fluid pathways 334, 336 and 338 may be fluidly coupled to the conduit 310 by the adapter 312. For example, the negative pressure pathway 336 may be fluidly coupled to the central lumen 328 so that the negative pressure pathway 336 functions to deliver negative pressure to the tissue interface 108. The pressure sensing pathways 334 and 338 may be fluidly coupled to the peripheral lumens 322 so that the pressure sensing pathways 334 and 338 function to sense negative pressure at the tissue interface 108. Each of the pressure sensing pathways 334 and 338 may be fluidly coupled directly to the peripheral lumens 322. In other embodiments, both of the sensing pathways 334 and 338 may be fluidly coupled to a single space within the adapter 312 that is also fluidly coupled to the peripheral lumens 322. In some example embodiments, the other end of the fluid pathways 334, 336 and 338 may terminate within the applicator 308 of the dressing interface 307 and be fluidly coupled to each other within the applicator 308 for delivering and sensing the negative pressure associated with the tissue interface 108.

The applicator 308 of the dressing interface 307 may comprise an opening or aperture 342 in the second layer 332 the applicator 308 adapted to fluidly couple the sealed space of the dressing interface 307 to the tissue interface 108. The aperture 342 along with the first layer 331 and second layer 332 portions of the applicator 308 may define a recessed space 344 within the sealed space of the applicator 308, wherein the recessed space 344 is adapted to be in fluid communication with the tissue interface 108 when disposed over the tissue site. That portion of the recessed space 344 covered by the second layer 332 of the applicator 308 may be referred to as a covered space 345. In some example embodiments, the walls 335 and 337 may extend only partially into the recessed space 344 so that the end of the walls 335 and 337 are exposed by the aperture 342 as shown in FIG. 3. In this embodiment, the pressure sensing pathways 334 and 338 are in fluid communication with the recessed space 344. The negative pressure pathway 336 is also in fluid communication with the recessed space 344 and is adapted to deliver negative pressure to the tissue interface 108 through the recessed space 344, while the pressure sensing pathways 334 and 338 are adapted to sense the pressure within the sealed environment. In some example embodiments, the walls 335 and 337 may extend beyond the aperture 342 (not shown) so that less of the pressure sensing pathways 334 and 338 are being exposed to the negative pressure being delivered to the tissue interface 108 by the negative pressure pathway 336 to avoid inclusions and/or blockages by fluids from the tissue site 1.

The dressing interface 307 may further comprise a plurality of features such as, for example, flexible projections, flexible standoffs, or closed cells such as, for example, closed cells 340 described in more detail below, having a bottom portion extending from the first layer 331 and a top portion extending within the sealed spaces toward the second layer 332 outside the recessed space 344. Within the recessed space 344, the top portion of the closed cells 340 extending from the first layer 331 may extend toward the tissue interface 108 and may be adapted to come in direct contact with the tissue interface 108 when the dressing interface 307 applies negative pressure to the tissue site. The features and the closed cells 340 provide a cushion to help prevent the sealed spaces of the dressing interface 307 from collapsing as a result of external forces as described above. In some example embodiments, the top portion of the closed cells 340 may come in contact with the second layer 332, and in some other example embodiments, the top portion of the closed cells 340 may be coupled to the second layer 332. In some example embodiments, the closed cells 340 may be disposed in the applicator 308 of the dressing interface 307, but not in the bridge 309 of the dressing interface 307 which may contain, for example, a fabric material instead of the closed cells 340. In some example embodiments, the features they comprise projections or nodes (not shown) having a flexibility similar to the closed cells 340.

The dressing interface 307 may also comprise an affixation surface 346 surrounding the aperture 342 in the applicator 308 of the second layer 332 that can be used to couple the dressing interface 307 to the tissue site. In some embodiments, a top drape (not shown) may be utilized to cover the applicator 308 of the dressing interface 307 to provide additional protection and support over the applicator 308 when the dressing interface 307 is applied to the tissue site. In some embodiments, the top drape may also be utilized to cover any adhesive that might be exposed from applying the dressing interface 307 to the tissue site. In some embodiments, the top drape may be similar to the cover 106 described above and, as such, may be a polymer such as a polyurethane film.

Figure 3B:
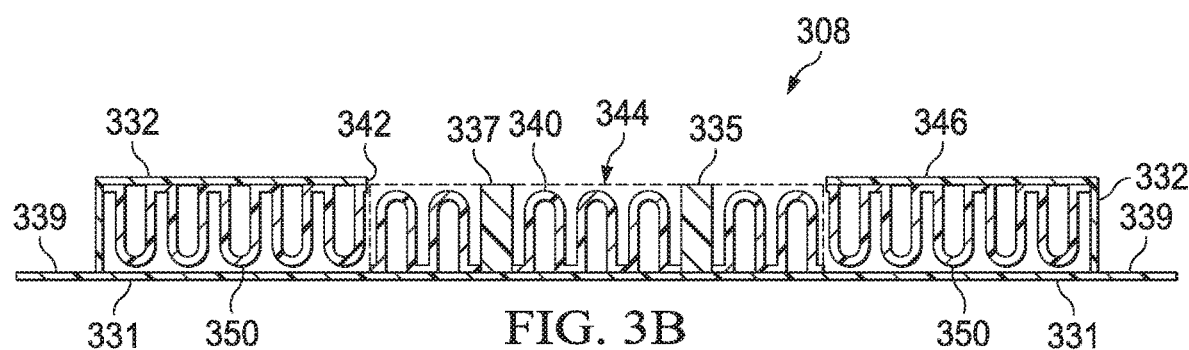
Figure 3C:
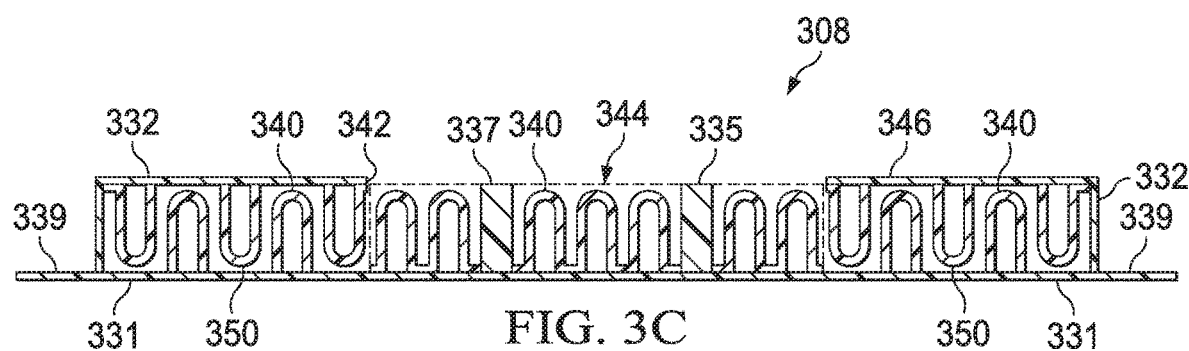

As indicated above with respect to the recessed space 344, the top portion of the closed cells 340 extend from the first layer 331 toward the tissue interface 108 through the aperture 342 of the second layer 332 and may be adapted to come in direct contact with the tissue interface 108. However, in the sealed spaces outside the recessed space 344, the dressing interface 307 may further comprise a plurality of features or closed cells having a bottom portion extending from the second layer 332 and a top portion extending within the sealed spaces toward the first layer 331. Referring for example to FIG. 3B, a cross-sectional view taken along line 3B-3B in FIG. 3 to show another possible example embodiment of the dressing interface 307 that comprises a plurality of features or closed cells 350 having a bottom portion extending from the second layer 332 and a top portion extending within the sealed spaces outside the recessed space 344 toward the first layer 331. However, within the recessed space 344, the top portions of the closed cells 340 still extend from the first layer 331 into the recessed space 344. Referring for example to FIG. 3C, a cross-sectional view taken along line 3C-3C in FIG. 3 to show yet another possible example embodiment of the dressing interface 307 that comprises both a plurality of closed cells 340 and a plurality of closed cells 350 extending from the first layer 331 and the second layer 332, respectively, within the sealed spaces outside the recessed space 344 toward the second layer 332 and the first layer 331, respectively. Again however, within the recessed space 344, the top portions of the closed cells 340 still extend from the first layer 331 into the recessed space 344.

In some example embodiments, the first layer 331 and the second layer 332, including the closed cells 340 and the closed cells 350 respectively, may be formed from a non-porous, polymeric film that may comprise any flexible material that can be manipulated to enclose closed cells, including various thermoplastic materials, e.g., polyethylene homopolymer or copolymer, polypropylene homopolymer or copolymer, etc. Non-limiting examples of suitable thermoplastic polymers include polyethylene homopolymers, such as low density polyethylene (LDPE) and high density polyethylene (HDPE), and polyethylene copolymers such as, e.g., ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches, including linear low density polyethylene (LLDPE), linear medium density polyethylene (LMDPE), very low density polyethylene (VLDPE), and ultra-low density polyethylene (ULDPE). Various other materials are also suitable such as, e.g., polypropylene homopolymer or polypropylene copolymer (e.g., propylene/ethylene copolymer), polyesters, polystyrenes, polyamides, polycarbonates, etc.

In some example embodiments, the first layer 331 and the second layer 332, including the closed cells 340 and the closed cells 350 respectively, may comprise a polymeric film such as, for example, a thermoplastic polyurethane (TPU) film that is permeable to water vapor but impermeable to liquid. The first layer 331 and the second layer 332 may be in various degrees breathable and may have MVTRs which are proportional to their thickness. For example, the MVTR may be at least 300 g/m$^2$ per twenty-four hours in some embodiments. For permeable materials, the permeability generally should be low enough to maintain a desired negative pressure for the desired negative therapy treatment.

In some example embodiments, the layer having the closed cells may be formed from two sheets of polymeric film having inner surfaces coupled together to form sealed regions defining the plurality of closed cells. When the dressing interface 307 is positioned at the tissue site and negative pressure is applied as described above, the closed cells formed by the polymeric film are structured so that they do not completely collapse from apposition forces resulting from the application of negative pressure and/or external forces to the dressing interface 307 and the tissue site. The two sheets of polymeric film may be a single sheet of material having two laminae or two separate sheets that are coupled together to form the closed cells. The sheets of polymeric film may initially be separate sheets that are brought into superposition and sealed or they may be formed by folding a single sheet unto itself with a heat sealable surface facing inward. Each sheet of the polymeric film also may be a monolayer or multilayer structure depending on the application or the desired structure of the closed cells.

As indicated above, it is desirable that the closed cells formed by the polymeric film are resistant to collapsing from the negative pressure when applied to the dressing interface 307 and the tissue site. In one embodiment, the polymeric film possesses sufficient tensile strength to resist stretching under the apposition forces created by negative pressure wound therapy. The tensile strength of a material is the ability of material to resist stretching as represented by a stress-strain curve where stress is the force per unit area, i.e., pascals (Pa), newtons per square meter (N/m$^2$), or pounds per square inch (psi). The ultimate tensile strength (UTS) is the maximum stress the material can withstand while being stretched before failing or breaking. Many materials display a linear elastic behavior defined by a linear stress-strain relationship often extending up to a nonlinear region represented by the yield point, i.e., the yield strength of a material. For example, high density polyethylene (HDPE) has a high tensile strength and low-density polyethylene (LDPE) has a slightly lower tensile strength, which are suitable materials for the sheets of non-porous, polymeric film as set forth above. Linear low density polyethylene (LLDPE) is often used as well because the material stretches very little as the force is increased up to the yield point of the material. Thus, the closed cells are able to resist collapsing (or stretching) when subjected to an external force or pressure. For example, HDPE has a UTS of about 37 MPa and may have a yield strength that ranges from about 26-33 MPa depending on the thickness of the material, while LDPE has somewhat lower values.

In some example embodiments, the first layer 331 and the second layer 332, including the closed cells 340 and the closed cells 350 respectively, may comprise a thermoplastic polyurethane (TPU) film as described above. The thermoplastic polyurethane film may be, for example, a Platilon® thermoplastic polyurethane film available from Convestro LLC, that may have a UTS of about 60 MPa and may have a yield strength of approximately 11 MPa or greater than about 10 MPa depending on the thickness of the material. Therefore, in some example embodiments, it is desirable that the non-porous, polymeric film may have a yield strength greater than about 10 MPa depending on the type and thickness of material. A material having a lower yield strength may be too stretchable and, therefore, more susceptible to breaking with the application of small amounts of compression and/or apposition forces.

Figure 4:
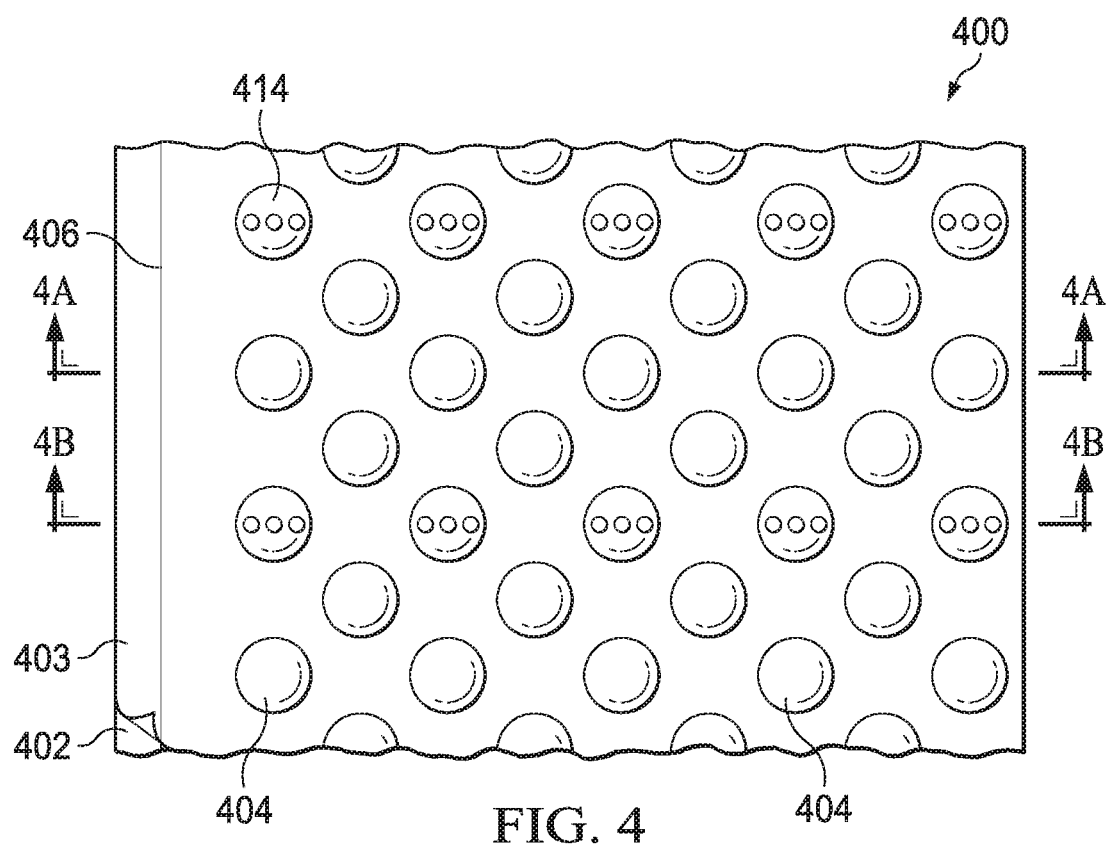
FIG. 4 is a plan view of a first embodiment of one of the first and second layers of the first dressing interface that include closed cells formed from a web of polymeric film that may be used as a component of the first dressing interface of FIG. 3.

FIG. 4 is a plan view of a first embodiment of one of the first and second layers of the first dressing interface that include closed cells formed from a web of polymeric film that may be used as a component of the first dressing interface of FIG. 3. More specifically, FIG. 4 shows one example embodiment of either one of the first layer 331 and the second layer 332, whichever one has the closed cells 340 or 350, i.e., layer 400. In some example embodiments, the layer 400 may comprise two sheets of polymeric film, i.e., sheet 402 and sheet 403. A portion of each of the sheets 402 and 403 may have inner surfaces coupled to each other to form a sealed region 406 that defines a plurality of closed cells 404 in the remaining portion of the sheets 402 and 403. The closed cells 404 and the sealed region 406 may be formed from a process such as, for example, vacuum forming. In some embodiments, the sealed region 406 may be formed by a heat seal between the inner surfaces of the sheets 402 and 403, while the closed cells 404 may be formed simultaneously by vacuum forming. In another example embodiment, the sealed region 406 may be formed by adhesion between the sheets 402 and 403. Alternatively, sheets 402 and 403 may be adhesively bonded to each other. The sealed region 406 may be flexible enough so that the dressing interface 307 is sufficiently flexible to conform to the shape the tissue site. The sealed region 406 may be sufficiently flexible or sized so that the dressing interface 307 may be folded to conform to the tissue site to provide optimal negative pressure to the tissue site.

In some example embodiments, the closed cells 404 may be substantially airtight to inhibit collapsing of the closed cells 404 from the application of negative pressure which could block the flow of fluid through the dressing interface 307 as described above. The closed cells 404 may be substantially airtight when formed and have an internal pressure that is an ambient pressure. In another example embodiment, the closed cells 404 may be inflated with air or other suitable gases such as, for example, carbon dioxide or nitrogen. The closed cells 404 may be inflated to have an internal pressure greater than the atmospheric pressure to maintain their shape and resistance to collapsing under pressure and external forces. For example, the closed cells 404 may be inflated to a pressure up to about 25 psi above the atmospheric pressure so that they do not collapse as described above.

The polyurethane film may have a thickness within a range of 400 to 600 microns. In some example embodiments, the first layer 33 land the second layer 332, including the closed cells 340 and the closed cells 350 respectively, may be formed from thermoplastic polyurethane film having a thickness of 500 microns. In some example embodiments, the individual sheets 402 and 403, prior to fabricating either one of the first layer 331 or the second layer 332, may each have a thickness of about 200 µm to about 600 µm. In some embodiments, the individual sheets 402 and 403 may each have a thickness of about 250 µm. In some other embodiments, the individual sheets 402 and 403 may each have a thickness of about 500 µm. In some embodiments, the thickness of the layer that does not have closed cells may be up to 50% thinner than the thickness of the layer that that includes the closed cells. For example, referring to FIG. 3A, the thickness of the second layer 332 without any closed cells may be up to 50% thinner than the thickness of the first layer 331 that has the closed cells 340. After the layers have been fabricated, the sealed region 406 may have a thickness between about 800 μm and about 1200 μm. If the fabrication process comprises injection molding, the closed cells 404 may have a thickness between about 400 μm and about 500 μm. However, if the closed cells 404 are fabricated by drawing the polyurethane film to form the closed cells 404, the top portion of the closed cells 404 may have a thickness as thin as 50 μm.

After the closed cells 404 have been fabricated, the walls of the closed cells 404 may have a thickness relative to the thickness of the individual sheets 402 and 403 as defined by a draw ratio, i.e., the ratio of the average height of the closed cells 404 to the average thickness of the sheets 402 and 403. In some example embodiments, the closed cells 404 may have a generally tubular shape as described above that may have been formed from the sheets 402 and 403 having various thicknesses and draw ratios. In some example embodiments, the sheets 402 and 403 may have an average thickness of 500 μm and the closed cells 404 may have an average height in a range between about 2.0 mm and 5.0 mm. Consequently, the closed cells 404 may have a draw ratio ranging from about 4:1 to about 10:1 for heights of 2.0 and 5.0 mm, respectively. In another example embodiment, the draw ratio may range from about 5:1 to about 13:1 where the thickness of the sheets 402 and 403 is an average of about 400 μm. In yet another example embodiment, the draw ratio may range from about 3:1 to about 9:1 where the thickness of the sheets 402 and 403 is an average of about 600 μm. In some embodiments, the closed cells 404 may have an average height in a range between about 1.0 mm and 4.0 mm depending on the thickness of the sheets 402 and 403. The sheets 402 and 403 may each have the same or different thicknesses and flexibilities, but are substantially non-stretchable as described above so that the closed cells 404 maintain a generally constant volume without bursting after a compression force is applied to the dressing interface 307 or negative pressure is applied to the dressing interface 307 and the tissue site. Consequently, even when a load is applied to the dressing interface 307 which squeezes the closed cells 404 into a different shape, the closed cells 404 are sufficiently flexible to recover their original shape after being squeezed without bursting.

Figure 4A:
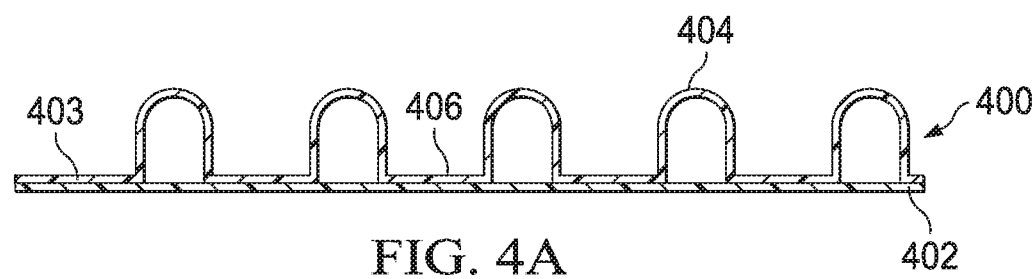
FIGS. 4A and 4B are cross-sectional views taken along lines 4A-4A and 4B-4B in FIG. 4 of a first and second embodiment of the closed cells.

The sealed region 406 may define the base or the cross-sectional shape of the closed cells 404 as being generally circular as shown, but in other embodiments may define the base as being a rectangular or triangular shape, hexagonal, or other geometric or an irregular shape. The closed cells 404 may be formed with a volumetric shape corresponding to the cross-sectional shape of the closed cells 404. For example, the volumetric shape may be generally hemispherical in shape as shown. In other example embodiments, the closed cells 404 may be formed with a volumetric shape that is generally conical, cylindrical, tubular having a flattened or hemispherical end, or geodesic shape. These volumetric shapes may be formed in either one of the sheets 402 and 403 such as the tubular shape of the closed cells 404 shown in FIG. 4A. The closed cells 404 may be tubular shapes formed with generally parallel walls extending from the sealed region 416 to a hemispherical or flat top portion of the closed cells 404. Alternatively, the walls of the closed cells 404 may taper or expand outwardly from the sealed region 416 to the top portion so that the diameter of the top portion of the closed cells 404 is larger than at the base of the closed cells 404.

In some embodiments, the closed cells 404 that are generally hemispherical or tubular in shape may have a diameter between about 1.0 mm and about 10 mm. In some other embodiments, the closed cells 404 may have a diameter between about 2.0 mm and about 5.0 mm. In some embodiments, the closed cells 404 also may have a pitch, i.e., the center to center distance between each of the closed cells 404, between about 1 mm and 10 mm. In some other embodiments, the closed cells 404 may also have a pitch between about 2 mm and about 3 mm. Because the sealed region 406 defines the base of the closed cells 404 including the diameter of a circular base and the pitch of closed cells 404, the surface area of the layer 400 covered by the closed cells 404 may also be determined as a percentage, i.e., the cell coverage percentage. In one example embodiment wherein the diameter of the closed cells 404 is about 1.0 mm and the pitch is about 2.0 mm, the cell coverage percentage is about 22% of the surface area of the layer 400. In another example embodiment wherein the diameter of the closed cells 404 is about 2.0 mm and the pitch is about 5.0 mm, the cell coverage percentage is about 14% of the surface area of the layer 400. In yet another example embodiment wherein the diameter of the closed cells 404 is about 1.5 mm, the pitch is about 2.0 mm, and the closed cells 404 are more tightly arranged such that there are about 28.5 cells in a 10 $mm^2$ section of the layer 400, the cell coverage percentage is about 51% of the surface area of the layer 400. Depending on the diameter, pitch, and arrangement of the closed cells 404, the cell coverage percentage may range between about 10% and about 60% of the surface area of either one of the layers having the closed cells such as layer 400. Closed cells 404 having other base shapes or volumetric shapes also may have a cell coverage percentage in generally the same range.

Figure 4B:
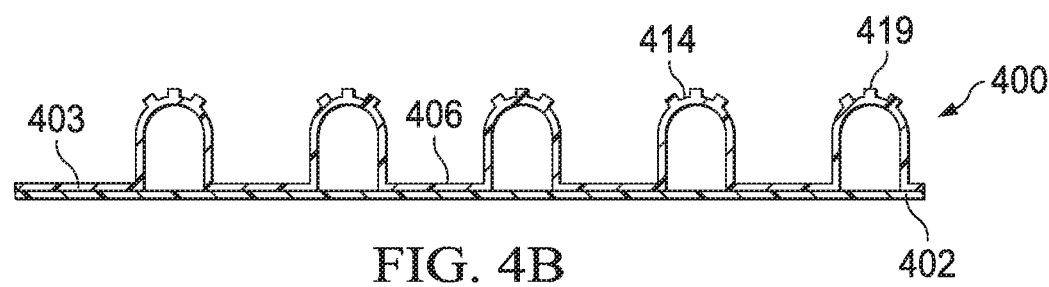

When the dressing interface 307 is disposed at the tissue site, a portion of the closed cells 340 may extend through the recessed space 344 and the aperture 342 of the dressing interface 307 to contact the tissue interface 108 as described above. A portion of those closed cells 340 extending through the recessed space 344 may be textured with surface features, which may be protrusions or indentations, to enhance fluid flow through the dressing interface 307 to the tissue interface 108 and the tissue site. In one exemplary embodiment as shown in FIG. 4B, closed cells 414 may be embossed with projections or nodes so that the nodes 419 contact the on top of the closed cells 414 contact the tissue interface 108 to enhance fluid flow to tissue site. The nodes 419 may be projections that are flexible or rigid. In one embodiment, the projections may be formed from a substantially gas impermeable material such as silicone. In another embodiment, the projections may be formed from a semi-gas permeable material. The projections may be formed as an integral part of the sheet 403 and, therefore, they may also be formed from the same material as described above. In one embodiment, the projections may be solid, while in another embodiment the projections may be hollow to increase flexibility. The projections may form a plurality of channels and/or voids as described below to distribute reduced pressure and allow for fluid flow among the projections. The projections may be dimensioned to provide local load points evenly distributed at the tissue interface 108. The pattern and position of the projections may be uniform or non-uniform. The projections may have different shapes including, for example, the shape of a spike, cone, pyramid, dome, cylinder or rectangle.

Figure 5:
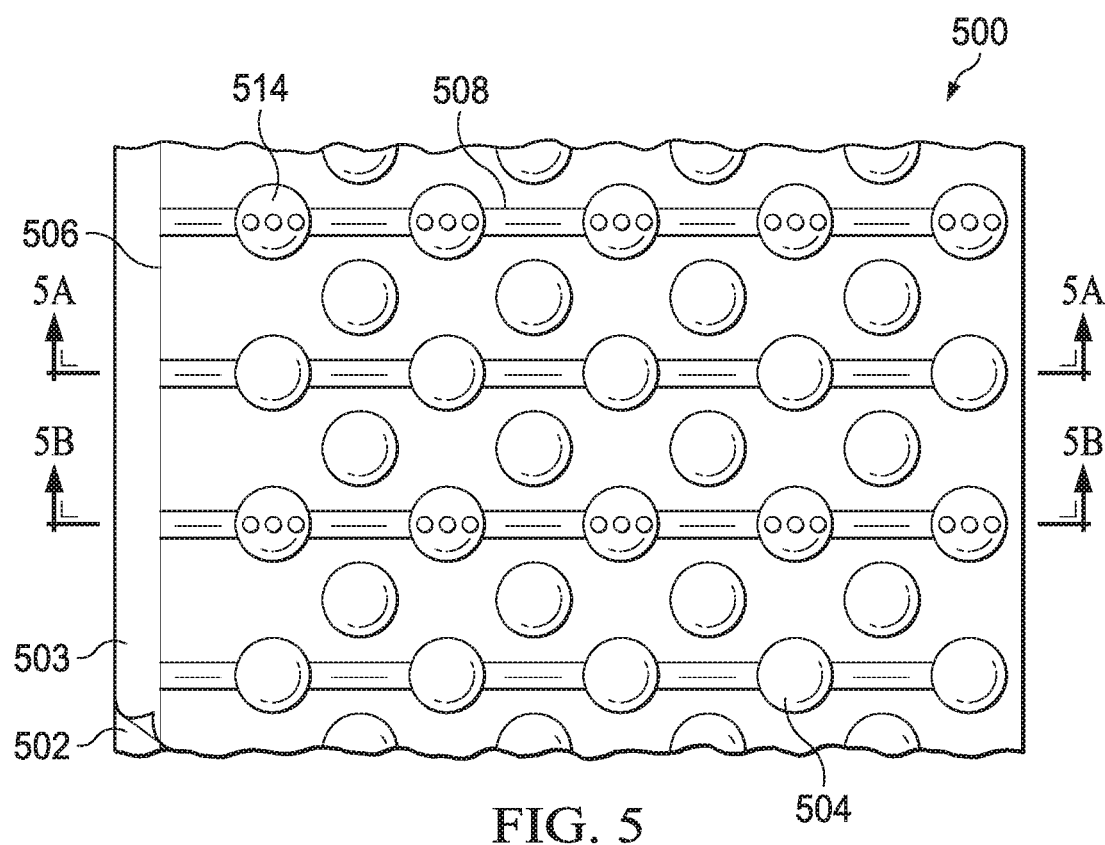
FIG. 5 is a plan view of a second embodiment of one of the first and second layers of the second dressing interface that include closed cells formed from a web of polymeric film that may be used as a component of the first dressing interface of FIG. 3.
Figure 5A:
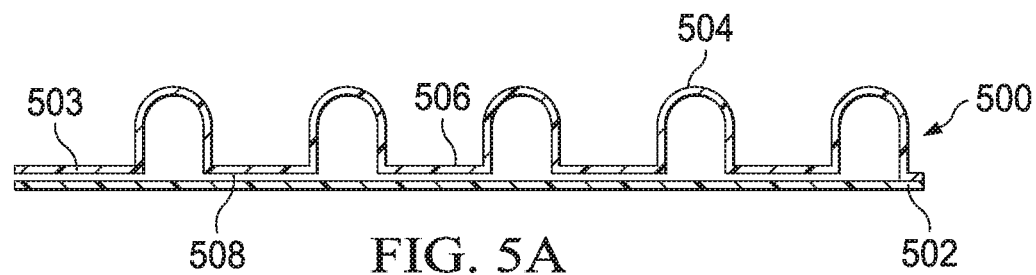
FIGS. 5A and 5B are cross-sectional views taken along lines 5A-5A and 5B-5B in FIG. 5 of a first and second embodiment of the closed cells.
Figure 5B:
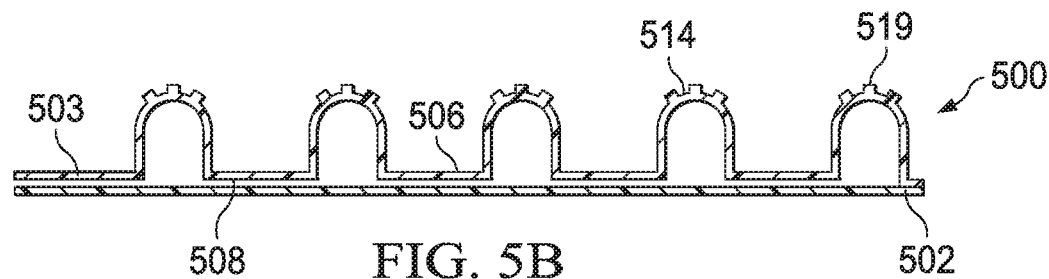

In some other illustrative embodiments, the layer 400 may further comprise chambers formed between closed cells to better distribute the apposition force applied to the manifold 400 as a result of the application of negative pressure because the volume of the chambers is greater than the volume of the individual closed cells. In one exemplary embodiment shown in FIGS. 5 and 5A, a layer 500 is similar in all respects to the layer 400 comprising two sheets 502 and 503 of polymeric film having inner surfaces coupled to each other in a pattern defining a plurality of closed cells 504. The sheets 502 and 503 may be sealed to each other to form a sealed region 506 defining the closed cells 504. The layer 500 also may comprise a plurality of passageways 508 fluidly coupling at least two of the closed cells 504 to form a closed chamber. In one exemplary embodiment, a closed chamber is formed by all of the closed cells 504 in a row fluidly coupled by the passageways 508 as shown in FIG. 5. The closed chambers may be formed in alternating rows as also shown in FIG. 5. The formation of closed chambers with closed cells in any pattern distributes apposition forces applied to the layer 500 more equally across the layer 500. A portion of those closed cells 504 and 514 extending through the recessed space 344 also may be textured with surface features, which may be protrusions or indentations, to enhance fluid flow through the dressing interface 307 to the tissue interface 108 and the tissue site as described above. In one exemplary embodiment as shown in FIG. 5B, closed cells 514 may be embossed with projections or nodes so that the nodes 519 contact the on top of the closed cells 514 contact the tissue interface 108 to enhance fluid flow to tissue site.

The layers 400 and 500 both comprise two sheets 402, 403 and 502, 503 of polymeric film having inner surfaces sealed to each other in a pattern defining a plurality of closed cells 404 and 504 in close proximity to one another. The sheets 402, 403 and 502, 503 may be sealed to each other in a sealed region 406 and 506 that defines the closed cells 404, 414 and 504, 514. In both embodiments, the rows of the closed cells 404, 414 and 504, 514 are staggered so that the individual cells may be more closely nested together between the alternating rows to form a nested pattern of cells formed on the same plane as defined by the sealed regions 406, 506, respectively. In other embodiments, the closed cells may be arranged in other patterns suitable for the particular therapy being utilized. For example, the rows and columns of the closed cells 404, 414 and 504, 514 may be arranged in line to form an aligned, rectangular pattern so that there is more spacing between the closed cells. Increasing the spacing between the closed cells may increase fluid flow within the fluid pathways of the dressing interface 307, whereas the nested arrangement of closed cells may restrict fluid flow within the fluid pathways. Referring back to FIG. 3, for example, the closed cells 340 disposed in the negative pressure pathway 336 are arranged in an aligned pattern that may increase fluid flow of negative pressure being applied to the tissue interface 108 to facilitate the removal of fluids and exudates within the recessed space 344. However, the closed cells 340 disposed in the pressure sensing pathways 334 and 338 are arranged in a nested pattern to facilitate pressure sensing within the recessed space 344 while impeding the inflow of fluids and exudates into the sensing pathways 334 and 338 to reduce the possibility of blockage.

In other example embodiments, the size and pitch of the closed cells also may be varied to effect change in the fluid flows through the fluid passageways. Referring again to FIG. 3, for example, the closed cells 340 disposed in the negative pressure pathway 336 have a slightly larger diameter and pitch than the closed cells 340 disposed in the pressure sensing pathways 334 and 338 that may increase fluid flow of negative pressure being applied to the tissue interface 108 to facilitate the removal of fluids and exudates within the recessed space 344. The closed cells 340 disposed in the pressure sensing pathways 334 and 338 have a slightly smaller diameter and pitch that may restrict fluid flow to facilitate pressure sensing within the recessed space 344 while impeding the inflow of fluids and exudates into the sensing pathways 334 and 338 to avoid blockages.

Figure 6:
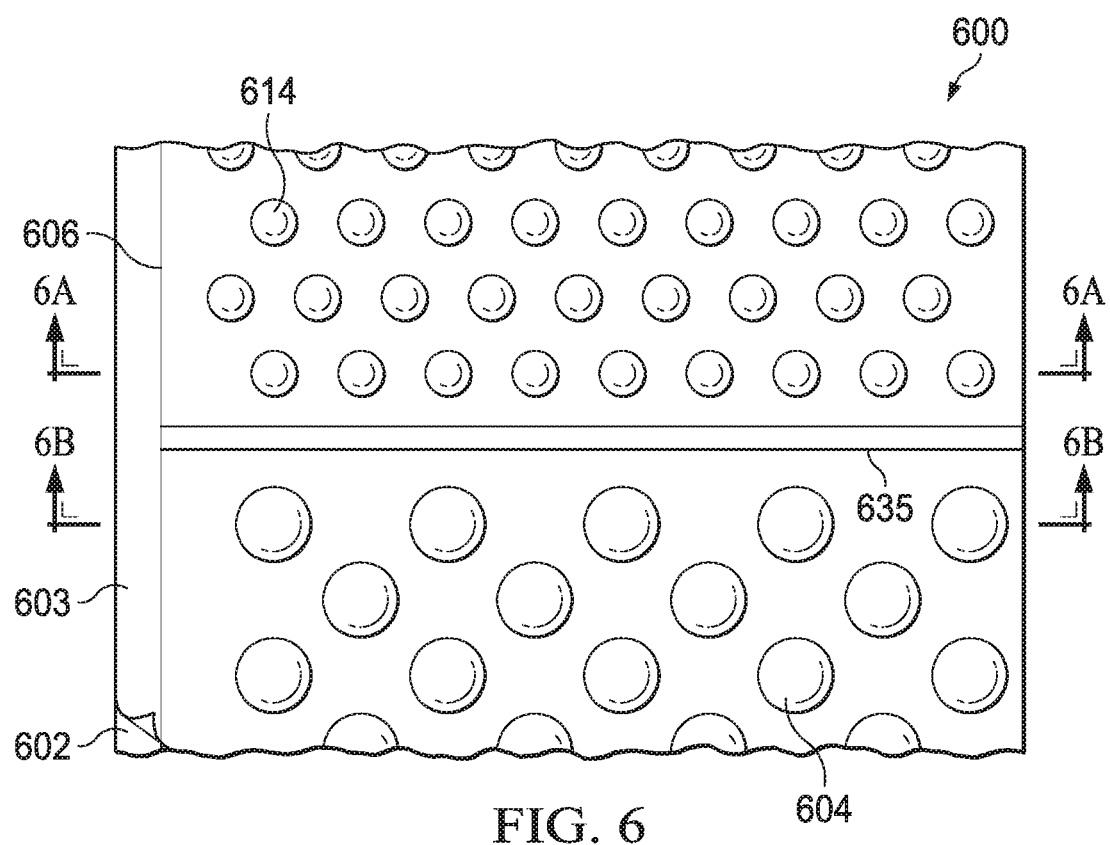
FIG. 6 is a plan view of a third embodiment of one of the first and second layers of the third dressing interface that include closed cells formed from a web of polymeric film that may be used as a component of the third dressing interface of FIG. 3.
Figure 6A:
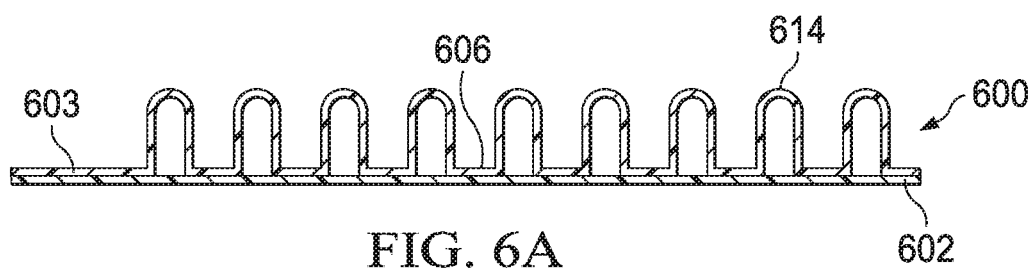
FIGS. 6A and 6B are cross-sectional views taken along lines 6A-6A and 6B-6B in FIG. 6 of a first and second embodiment of the closed cells.
Figure 6B:
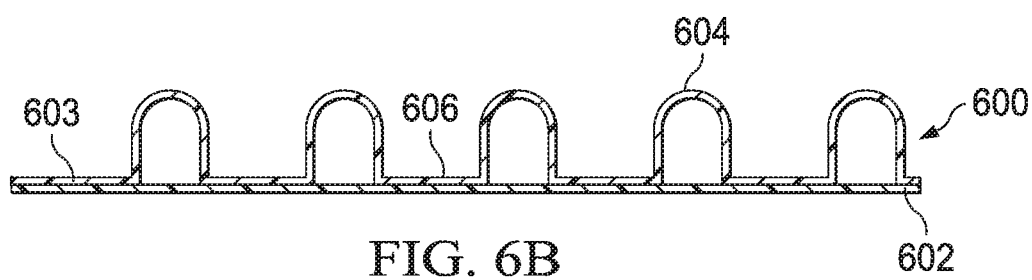

In yet another example embodiment as shown in FIGS. 6, 6A, and 6B, a closed-cell layer 600 also comprises two sheets 602 and 603 of polymeric film having inner surfaces sealed to each other in a pattern defining a plurality of closed cells in a nested arrangement including closed cells 604 and smaller closed cells 614. The sheets 602, 603 may be sealed to each other in a sealed region 606 that defines the closed cells 604, 614. In some embodiments, a wall 635 similar to the first wall 335 shown in FIG. 3 may be disposed between the plurality of closed cells 604 and 614 forming the negative pressure pathway 336 and the pressure sensing pathway 334, respectively. As can be seen, the closed cells 604 disposed in the negative pressure pathway 336 have a noticeably larger diameter and pitch than the smaller closed cells 614 that may increase fluid flow of negative pressure being applied to the tissue interface 108 to facilitate the removal of fluids and exudates within the recessed space 344. For example, the larger closed cells 604 may have a diameter in the range between about 1 mm and about 10 mm, whereas the smaller closed cells 614 may have a diameter in the range between about 1 mm and about 3 mm. The closed cells 614 disposed in the pressure sensing pathway 334 have a noticeably smaller diameter and pitch than the larger closed cells 604 that may restrict fluid flow to facilitate pressure sensing within the recessed space 344 while impeding the inflow of fluids and exudates into the pressure sensing pathway 334. It should be understood that the arrangement and dimensions of the closed cells may be tailored to manage the delivery of negative pressure to the tissue interface 108 and the measurement of pressure within the recessed space 344.

Figure 7:
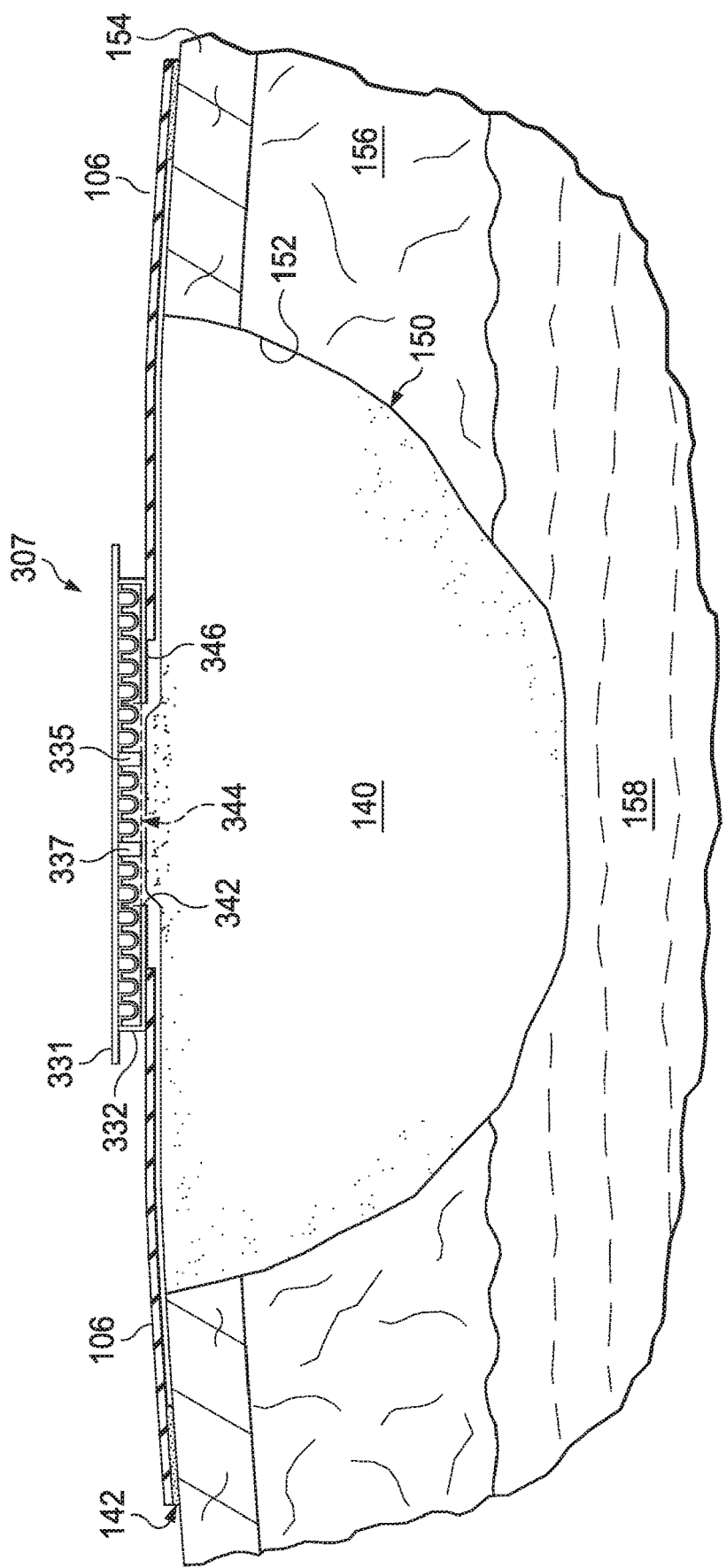
FIG. 7 is a schematic diagram of an example embodiment of the negative-pressure portion of the therapy system of FIG. 1 for delivering negative pressure to a dressing at a tissue site including a cover and the dressing interface of shown in FIG. 3.

In operation, the tissue interface 108 may be placed within, over, on, or otherwise proximate a tissue site, such as tissue site 150 as shown in FIG. 2 and described above. The cover 106 may be placed over the tissue interface 108 and sealed to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. FIG. 7 is a schematic diagram of another example embodiment of the negative-pressure portion of the therapy system of FIG. 1 for delivering negative pressure to a dressing at a tissue site including the cover 106 disposed over the tissue site 150, an attachment device 142 coupling the cover 106 to the tissue site 150, and the dressing interface 307 shown in FIG. 3. Additionally, the tissue interface 108 is the manifold 140 that may be in fluid communication with the recessed space 344 through the aperture 342 of the dressing interface 307 as described above and shown in FIG. 7. The affixation surface 346 of the dressing interface 307 may be coupled to the cover 106 to seal and fluidly couple the recessed space 344 of the dressing interface 307 to the manifold 140. The first wall 335 and the second wall 337 form the three sealed spaces or fluid pathways 334, 336 and 338 (as indicated by the dashed line arrows in FIG. 3) between the first layer 331 and the second layer 332 as described above.

As described above, the closed cells 340 have a bottom portion extending from the first layer 331 and a top portion extending within the sealed spaces toward the second layer 332 outside the recessed space 344. Within the recessed space 344, the top portion of the closed cells 340 extend from the first layer 331 toward the manifold 140 and may be adapted to come in direct contact with the manifold 140 when the dressing interface 307 applies negative pressure to the tissue site 150. When negative pressure is applied to the manifold 140, the dressing interface 307 is compressed as a result of an apposition force that causes the first layer 331 and the second layer 332 to collapse toward each other because of the vacuum created within the spaces between the closed cells 340. Although apposition forces may cause the closed cells 340 to change shape or flatten somewhat during the application of negative pressure to the manifold 140, the volume of the closed cells 340 remains substantially constant and, as a result, maintains fluid flow through the negative pressure pathway 336 to continue providing negative pressure therapy to the tissue site 150 and measuring the pressure provided by the pressure sensing pathways 334 and 338. The closed cells 340 also provide a cushion to help prevent the sealed spaces of the dressing interface 307 from collapsing as a result of external forces as described above. The closed cells 340 disposed in the negative pressure pathway 336 may be sized and arranged in a pattern that may increase fluid flow of negative pressure being applied to the manifold 140 to facilitate the removal of fluids and exudates within the recessed space 344. The closed cells 340 disposed in the pressure sensing pathways 334 and 338 may be sized and arranged in a pattern to facilitate pressure sensing within the recessed space 344 while impeding the inflow of fluids and exudates into the sensing pathways 334 and 338 to reduce the possibility of blockages.

Figure 8A:
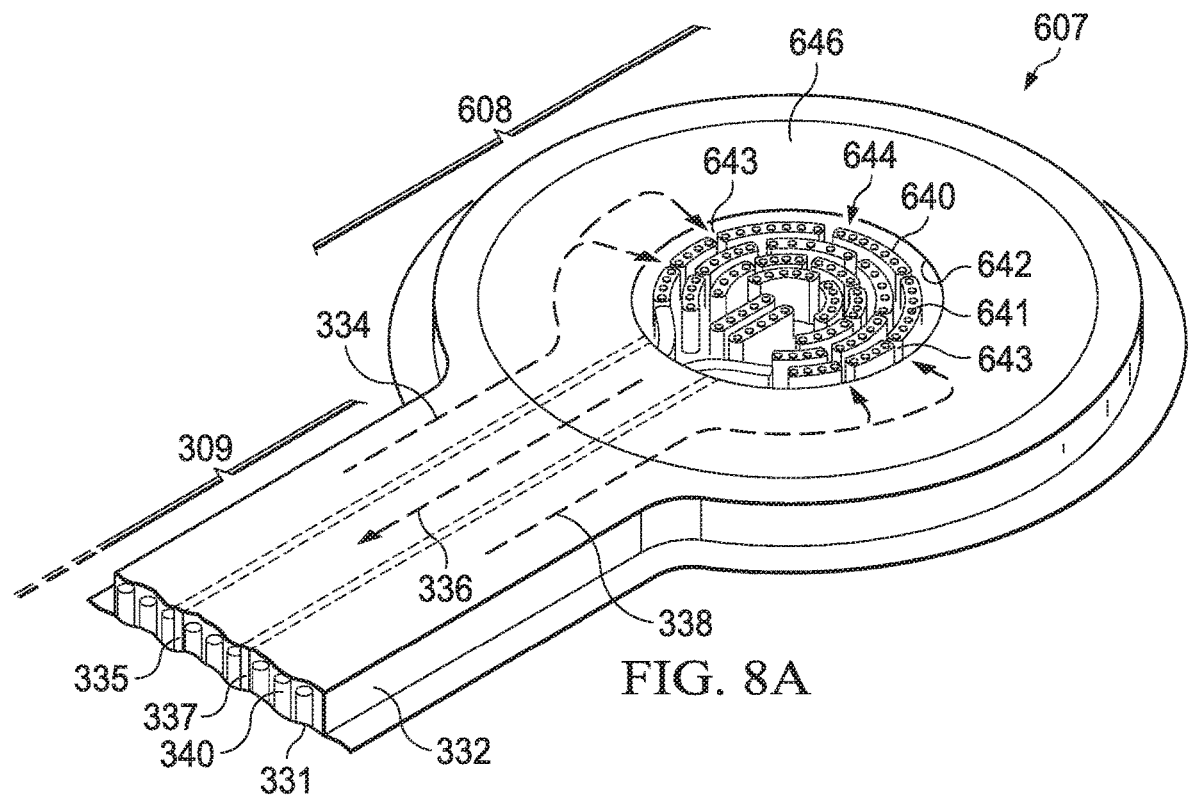
FIG. 8A is a segmented perspective bottom view of a applicator of a second dressing interface having a low profile structure that may be associated with some example embodiments of the therapy system of FIG. 1.
Figure 8B:
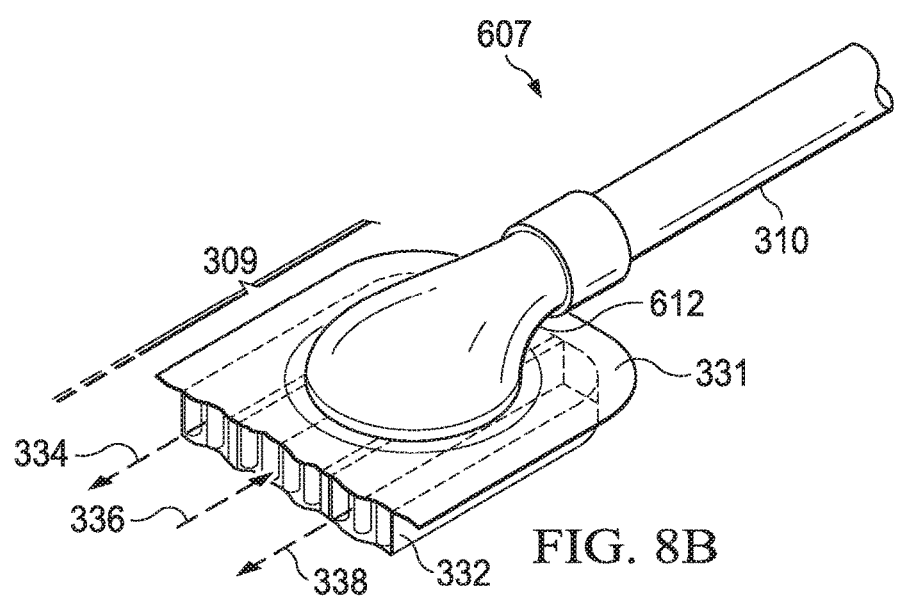
FIG. 8B is a segmented perspective top view of an adapter portion of the second dressing interface having a low profile structure that may be associated with some example embodiments of the therapy system of FIG. 1, i.e., the other end of the second dressing interface shown in FIG. 8A.
Figure 9:
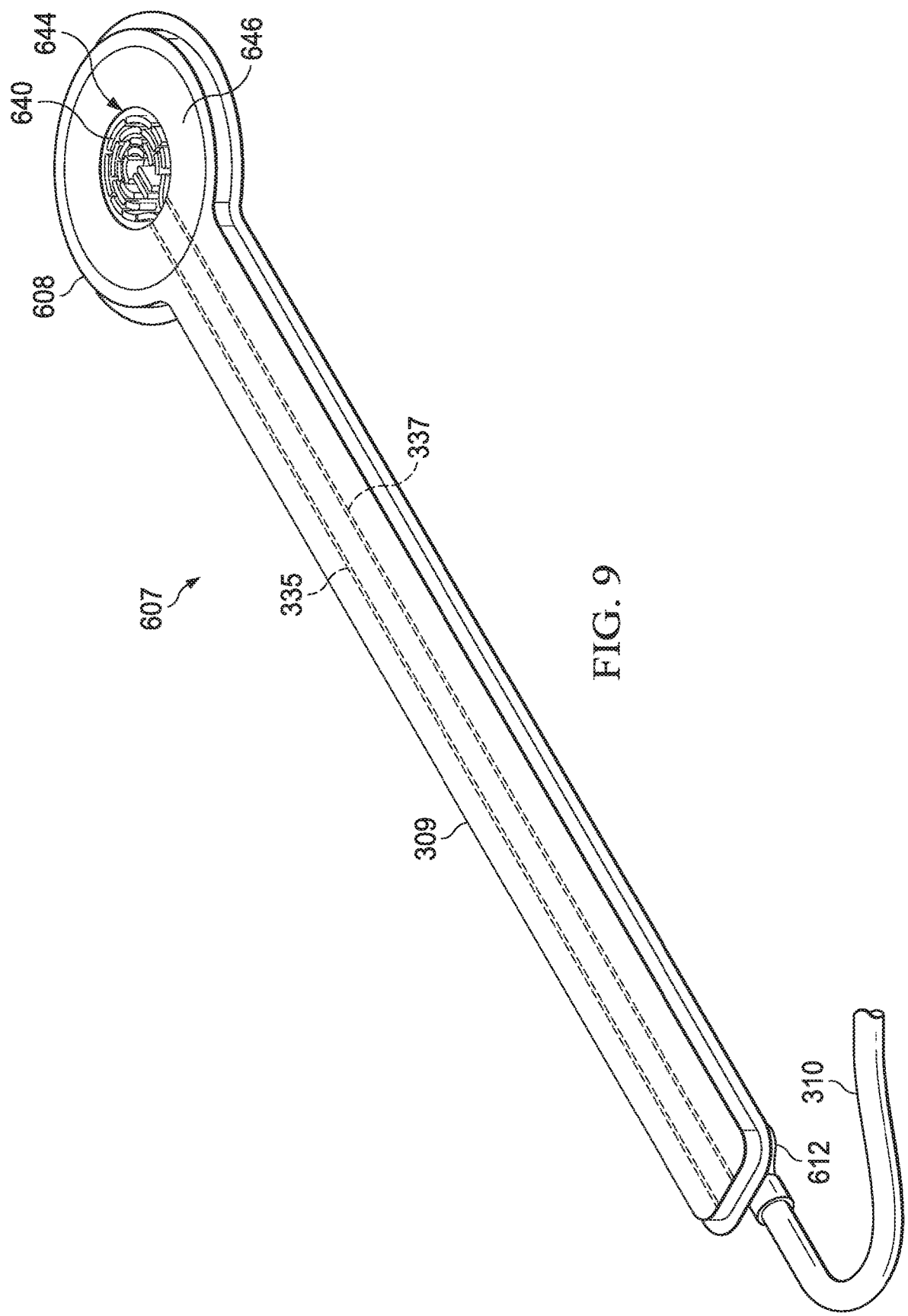
FIG. 9 is a perspective bottom view of the second dressing interface having a low profile structure that may be associated with some example embodiments of the therapy system of FIG. 1 including the bottom view shown in FIG. 8A.

As indicated above, the closed cells 340 of the dressing interface 307 may have a variety of shapes, and may be sized and arranged in different patterns within the sealed space to enhance the delivery of negative pressure to the tissue interface 108 or the manifold 140 for a specific type of tissue site while optimizing pressure sensing and measurement of the negative pressure within the recessed space 344. Another example embodiment of a dressing interface similar to the dressing interface 307 is shown in FIGS. 8A, 8B, and 9 as dressing interface 607 including components having reference numerals with the last two digits being substantially the same. The main differences between the two dressing interfaces are the applicator 308 and the adapter 312, i.e., the applicator 608 and an adapter 612 of the dressing interface 607. FIGS. 8A and 8B are segmented perspective views of the bottom and top of the dressing interface 607 having a low profile structure that may be associated with some example embodiments of the therapy system of FIG. 1. FIG. 9 is a perspective bottom view of the dressing interface 607 having a low profile structure that may be associated with some example embodiments of the therapy system of FIG. 1 including both the bottom view shown in FIG. 8A. The bridge 309 and the conduit 310 of the dressing interface 607 are substantially the same as the dressing interface 307. The adapter 612 may be functionally the same as the adapter 312, but has a different structure that may include a semi-rigid elbow connector having a low profile configuration. The applicator 608 may have a variety of shapes such as the rectangular shape of the dressing interface 307 or the circular shape of the dressing interface 607, depending on the one that is best suited for the tissue site and the pneumatic requirements of negative pressure delivery and pressure sensing.

Referring more specifically to FIGS. 8A and 9, the second layer 332 of the dressing interface 607 may have a generally circular aperture 642 that opens to a recessed space 644. A remaining portion of the second layer 332 in the applicator 608 may comprise an affixation surface 646 for attaching the dressing interface 607 to the tissue site. Additionally, the dressing interface 607 may further comprise a plurality of closed cells 640 having a generally elongated and convex shape that are arranged in a generally circular pattern disposed within the recessed space 644. The closed cells 640 may also comprise surface features 641 similar to the nodes 419 described above as shown in FIGS. 4 and 4B. The closed cells 640 disposed in the center of the recessed space 644 are more aligned with the negative pressure pathway 336 to increase fluid flow of negative pressure being applied to the tissue interface 108 to facilitate the removal of fluids and exudates within the recessed space 644. In some embodiments, some of the closed cells 640 may be disposed around the aperture 642 to form a semicircular path opposite the negative pressure pathway 336 including spaces or gaps 643 between the closed cells 640. The semicircular alignment of the closed cells 640 are positioned within the recessed space 644 to better avoid the flow of fluids passing through from the tissue interface 108 to the negative pressure pathway 336 when negative pressure is applied. Additionally, the gaps 643 are sufficiently small for further restricting fluid flow into the pressure sensing pathways 334 and 338 as indicated by the dashed arrows. The gaps 643 facilitate pressure sensing within the recessed space 644 while impeding the inflow of fluids and exudates into the sensing pathways 334 and 338 to reduce the possibility of blockage. In some embodiments, a portion of the aperture perimeter may be welded to the outer circle of the closed cells 640 to further restrict fluid flow to the pressure-sensing pathways 334 and 338 in order to further impede the inflow of fluids and exudates without inhibiting pressure sensing within the recessed space 644.

Figure 10:
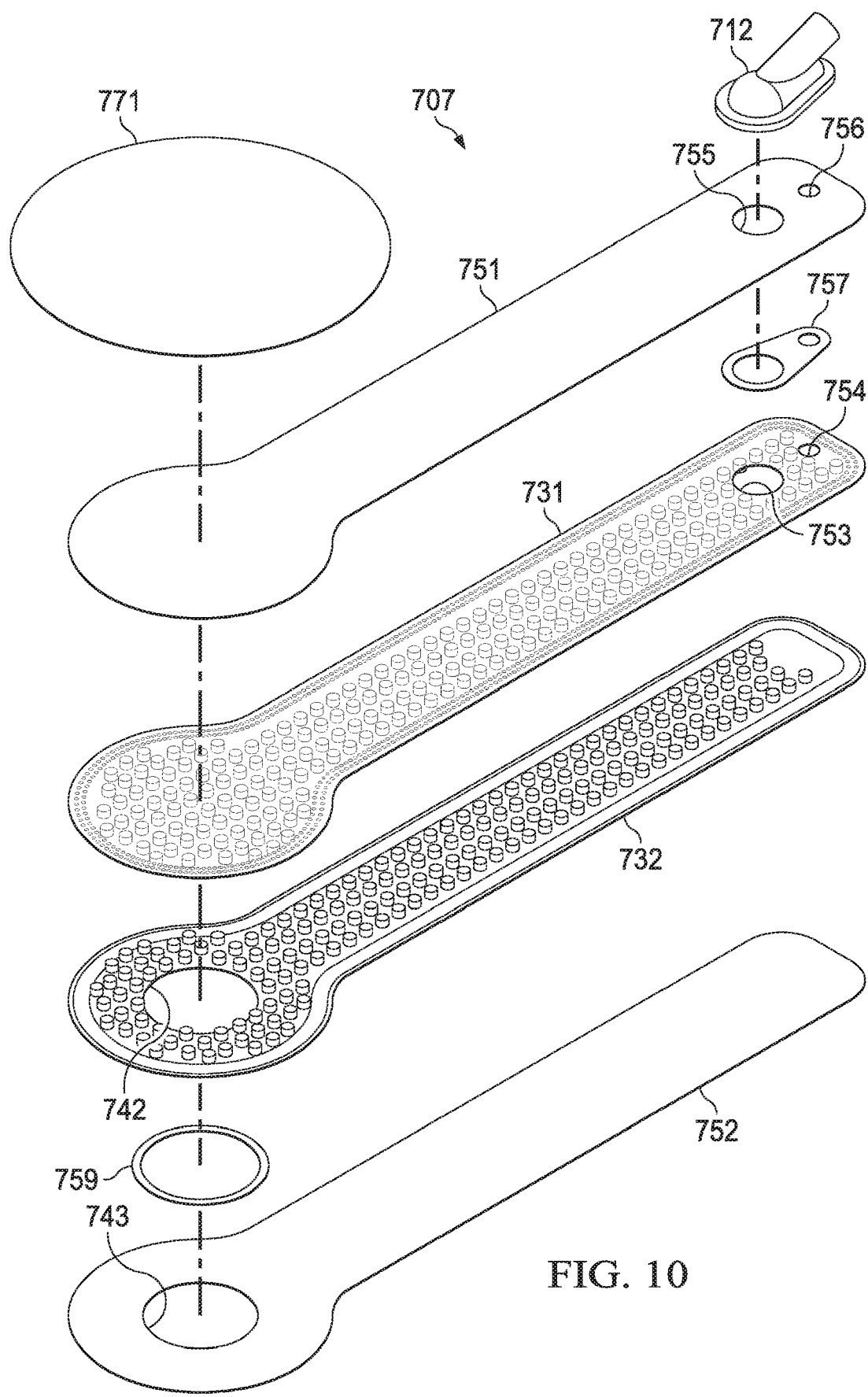
FIG. 10 is a perspective assembly view of a third dressing interface having a low profile structure that may be associated with some example embodiments of the therapy system of FIG. 1.
Figure 11A:
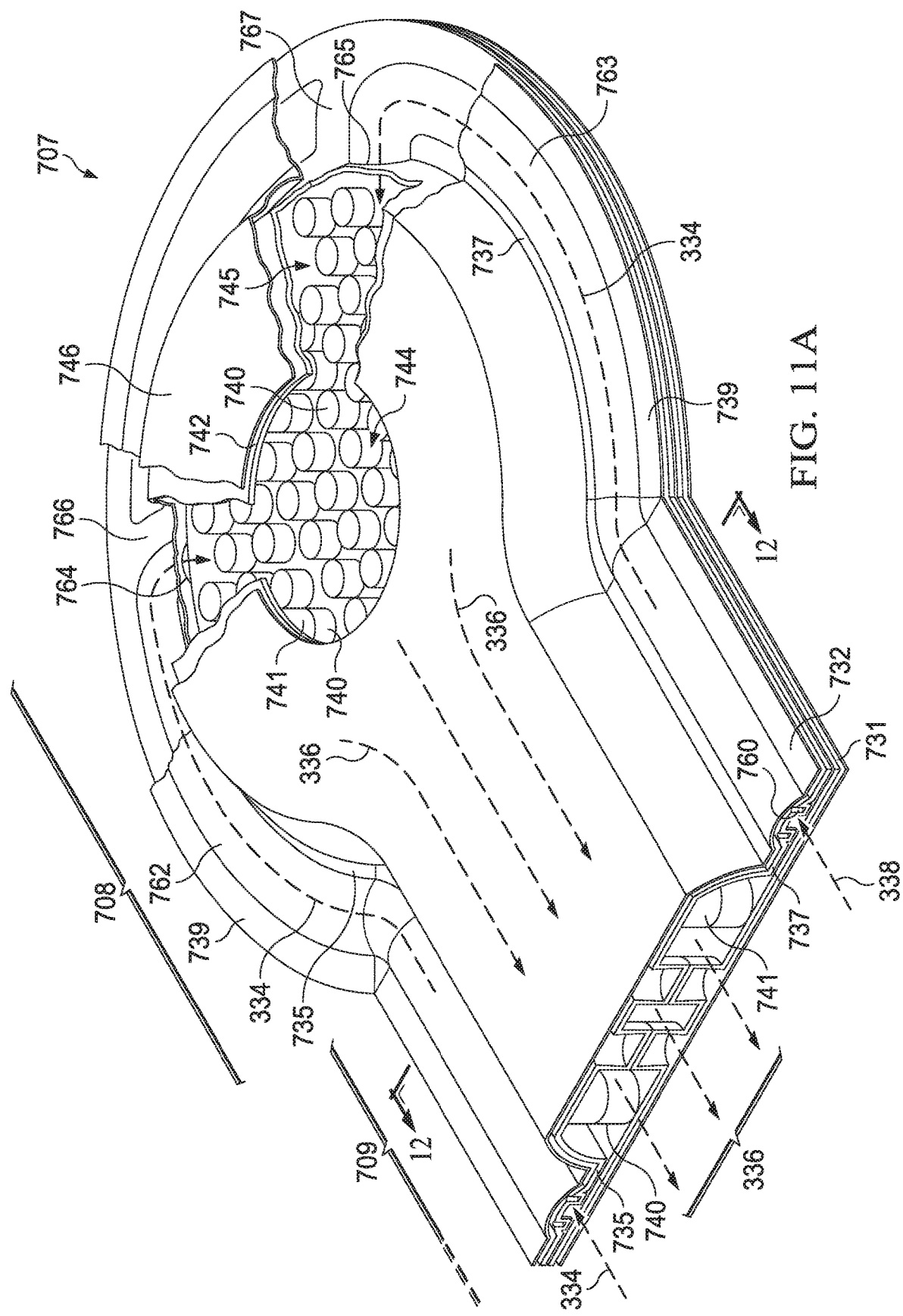
FIG. 11A is a segmented perspective bottom view of a applicator of the third dressing interface of FIG. 10.
Figure 11B:
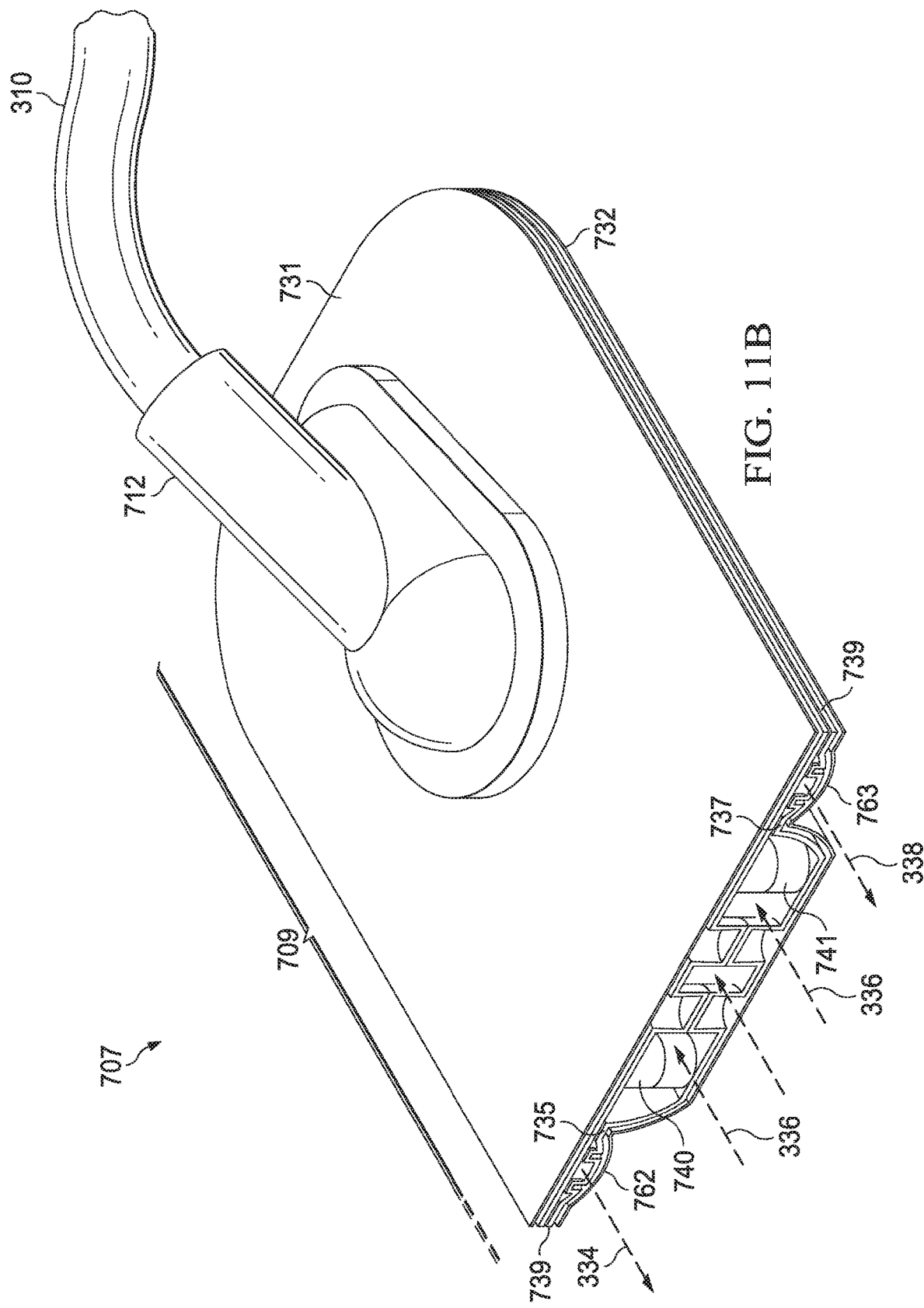
FIG. 11B is a segmented perspective top view of an adapter portion of the third dressing interface of FIG. 10, i.e., the other end of the third dressing interface.

As indicated above, the closed cells 340 of the dressing interface 307 and the dressing interface 607 may have a variety of shapes, and may be sized and arranged in different patterns within the sealed space to enhance the delivery of negative pressure to the tissue interface 108 or the manifold 140 for a specific type of tissue site while optimizing pressure sensing and measurement of the negative pressure within the recessed space 344 and the recessed space 644. Another example embodiment of a dressing interface similar to the dressing interface 307 and the dressing interface 607 is shown in FIGS. 10, 11A, 11B, 12 and 13 as dressing interface 707 including components having reference numerals with the last two digits being substantially the same. FIG. 10 is a perspective assembly view of the dressing interface 707 having a low profile structure that may be associated with some example embodiments of the therapy system of FIG. 1. FIGS. 11A and 11B are segmented perspective bottom and top views, respectively, of an applicator 708 and adapter 712 of the dressing interface 707 of FIG. 10. The dressing interface 707 like the dressing interface 307 also may comprise a bridge such as, for example, bridge 709 adapted for coupling the applicator 708 and the adapter 712 as shown in FIGS. 11A and 11B, respectively. The dressing interface 707 also may comprise a top layer such as, for example, a top layer 731 including a polymeric film and a base layer such as, for example, a base layer 732 coupled to the top layer 731 around the periphery of the top layer 731.

The adapter 712 of the dressing interface 707 may be functionally similar to the in-line adapter 312 as described above, or may be substantially similar to the elbow adapter 612 having a structure including a semi-rigid elbow port as shown in FIG. 11B. The applicator 708 of the dressing interface 707, like the dressing interface 307, may further comprise an opening or aperture 742 in the base layer 732 to fluidly couple the sealed space of the dressing interface 707 to the tissue interface 108. The aperture 742 along with the top layer 731 and the base layer 732 portions of the applicator 708 may define a recessed space 744 within the sealed space of the applicator 708, wherein the recessed space 744 is adapted to be in fluid communication with the tissue interface 108 when disposed over the tissue site. That portion of the recessed space 744 covered by the second layer 732 of the applicator 708 may be referred to as a covered space 745. In some embodiments, the aperture 742 may have a diameter in a range between about 3.25 cm and about 17.5 cm. The size of the aperture 742 is not a relatively small hole that must be aligned with the opening in the drape or cover 106 as in some prior art devices, but rather is sufficiently large along with the recessed space 744 to obviate the need for precise alignment or sizing. In some embodiments, the aperture 742 may even be larger than the opening in the cover 106. The dressing interface 707 may also comprise an affixation surface 746 surrounding the aperture 742 in the applicator 708 of the base layer 732 that may be used to couple the dressing interface 707 to the tissue site. In some embodiments, the attachment device 142 may be used to couple the affixation surface 746 to the tissue interface 108 and the tissue site. For example, the attachment device 142 may be an adhesive applied to the affixation surface 746, and covered by a release liner (not shown) to protect the adhesive prior to applying the dressing interface 707 to the tissue site.

The dressing interface 707 may further comprise at least one barrier or wall such as, for example, a first wall 735, coupled between the first layer 731 and the second layer 732. In some embodiments, the first wall 735 may extend from the end of the bridge 709 adjacent the adapter 712 into the applicator 708 to form at least two sealed spaces or fluid pathways between the first layer 731 and the second layer 732 within the dressing interface 707. In another example embodiment, the dressing interface 707 may further comprise a second barrier such as, for example, a second wall 737, coupled between the first layer 731 and the second layer 732. In some embodiments, the second wall 737 also may extend from the end of the bridge 709 adjacent the adapter 712 into the applicator 708. In some example embodiments, the first wall 735 and the second wall 737 may comprise a polymeric film coupled between the first layer 731 and the second layer 732. In some other example embodiments, the first wall 735 and the second wall 737 may comprise a weld (RF or ultrasonic), a heat seal, an adhesive bond, or a combination of any of the foregoing. In embodiments comprising two walls, e.g., the first wall 735 and the second wall 737, such embodiments may form three sealed spaces or fluid pathways within the sealed space between the first layer 731 and the second layer 732. In some embodiments, the first wall 735 and the second wall 737 cooperate with the flange 739 to form fluid conductors 762 and 763 for two of the fluid pathways that may be dedicated to measuring pressure such as, for example, pressure sensing pathways 334 and 338 (as indicated by the dashed line arrows), leaving one of the fluid pathways to be utilized for providing negative pressure such as, for example, negative pressure pathway 336 (as indicated by the dashed line arrows). In some example embodiments, the fluid conductors 762 and 763 may have a height having a value in a range between about 0.25 mm and about 3 mm. In some example embodiments, the fluid conductors 762 and 763 may have a width having a value in a range between about 1 mm and about 7.5 mm. Thus, the fluid conductors 762 and 763 may have a cross-sectional area having a value in a range between about 0.17 mm$^2$ and 16.77 mm$^2$. In some embodiments, the fluid conductors 762 and 763 may have a cross-sectional area having a value in a range between about 0.1 mm$^2$ and 18 mm$^2$.

In some example embodiments, the fluid conductors 762 and 763 and the fluid pathways 334, 336 and 338 may be fluidly coupled to the conduit 310 by the adapter 712. For example, the negative pressure pathway 336 may be fluidly coupled to the central lumen 328 so that the negative pressure pathway 336 functions to deliver negative pressure to the tissue interface 108. The pressure sensing pathways 334 and 338 may be fluidly coupled to the peripheral lumens 322 so that the pressure sensing pathways 334 and 338 function to sense negative pressure at the tissue interface 108. Each of the pressure sensing pathways 334 and 338 may be fluidly coupled directly to the peripheral lumens 322. In other embodiments, both of the sensing pathways 334 and 338 may be fluidly coupled to a single space (not shown) within the adapter 712 that is also fluidly coupled to the peripheral lumens 322. In some example embodiments, the other end of the fluid pathways 334, 336 and 338 may terminate within the applicator 708 of the dressing interface 707 for delivering and sensing the negative pressure associated with the tissue interface 108. In this embodiment of the bridge 709, both sensing pathways 334 and 338 are separate from, and side-by-side with, the negative-pressure pathway 336. The side-by-side orientation of the sensing pathways 334 and 338 with the negative-pressure pathway 336 forms a bridge that is generally flatter than a conduit or similar fluid conductor while still being resistant to collapsing under pressure that could block fluid flow through the fluid pathways.

Figure 12:
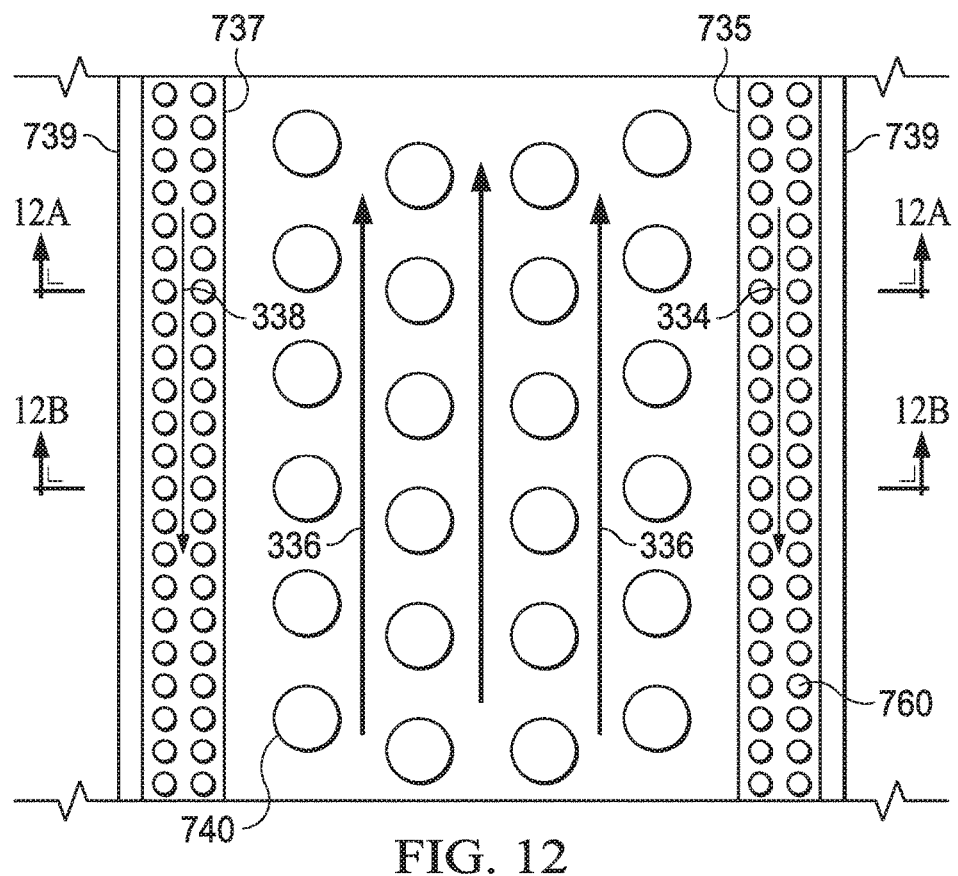
FIG. 12 is a plan view of a first embodiment of a bridge of the third dressing interface of FIG. 10, i.e., the bridge coupling the applicator and the adapter portion shown in FIGS. 11A and 11B, respectively.
Figure 13:
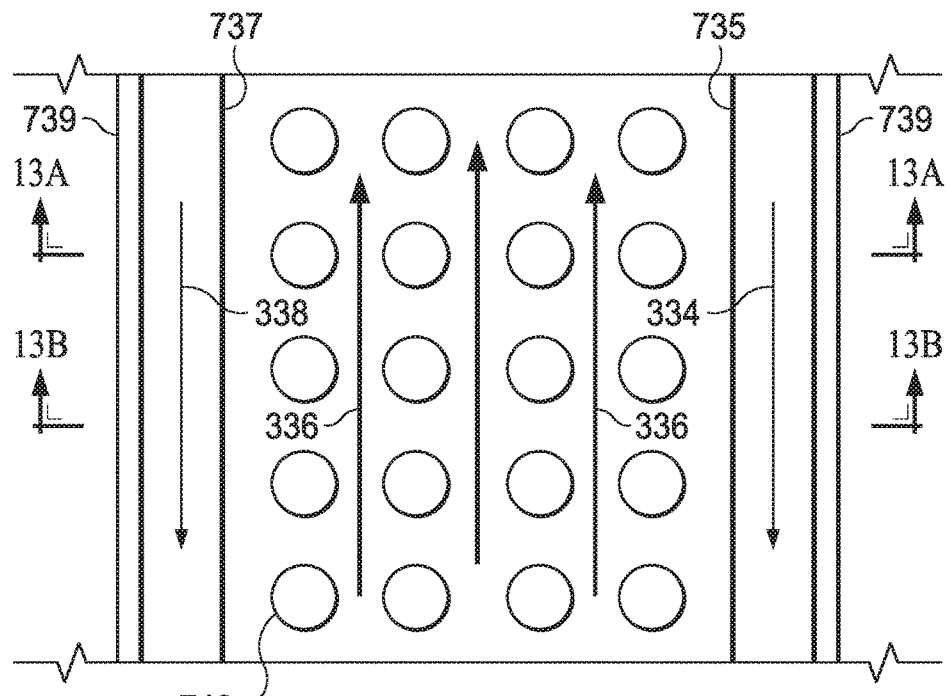
FIG. 13 is a plan view of a second embodiment of a bridge of the third dressing interface of FIG. 10, i.e., the bridge coupling the applicator and the adapter portion shown in FIGS. 11A and 11B, respectively.

In some example embodiments, each of the walls 735 and 737 may extend an angular distance around the proximal end of the applicator 708 and cooperate with blocking walls of the flanged 739 such as, for example, blocking walls 766 and 767, respectively, to form extensions of the fluid conductors 762 and 763, respectively, that may be fluidly coupled to the recessed space 744. In this embodiment, the pressure sensing pathways 334 and 338 are in fluid communication with the recessed space 744 through the fluid conductors 762 and 763 that may be fluidly coupled to the recessed space 744 by ports such as, for example, through-holes 764 and 765, respectively. In some example embodiments, In some embodiments, the fluid conductors 762 and 763 may include standoffs or closed cells 760 to form the pressure sensing pathways 334 and 338 as shown in FIG. 12. In other embodiments, the fluid conductors 762 and 763 may be opened and supported by a thicker base layer 732 as shown in FIG. 13. In still other embodiments, the fluid conductors 762 and 763 may comprise or be formed by tubes fluidly coupled to the pressure sensing pathways 334 and 338 in the bridge 709 and the through-holes 764 and 765. The negative pressure pathway 336 is also in fluid communication with the recessed space 744 and is adapted to deliver negative pressure to the tissue interface 108 through the recessed space 744, while the pressure sensing pathways 734 and 738 are adapted to sense the pressure within the sealed environment through the fluid conductors 762 and 763.

The angular distance of each of the walls 735 and 737 around the proximal end of the applicator 708 that form the fluid conductors 762 and 763 extends, for example, between about 45° and about 315° from the center of the negative pressure pathway 336 where the negative pressure pathway 336 is in fluid communication with the recessed space 744. In some embodiments, the angular distance may be different for each of the fluid conductors 762 and 763 as long as they are between about 45° and about 315° from the center of the negative pressure pathway 336. For example, the angular distance for each of the fluid conductors 762 and 763 may be located at about 60° and 210°, respectively, from the negative pressure pathway 336. In some example embodiments, the other ends of the fluid conductors 762 and 763 that are in fluid communication with the through-holes 764 and 765 are separated from each other by an angular distance of at least 90° extending around the applicator 708 in a direction away from the negative pressure pathway 336. The spacing and disposition of the through-holes 764 and 765 from each other, and from the negative pressure pathway 336, allows the pressure sensing pathways 334 and 338 to better avoid the flow of fluids passing through from the tissue interface 108 to the negative pressure pathway 336 when negative pressure is applied. Additionally, the through-holes 764 and 765 are sufficiently small for further restricting fluid flow into the fluid conductors 762 and 763 and the pressure sensing pathways 334 and 338 as indicated by the dashed arrows. In some embodiments, the through-holes 764 and 765 may have a cross-sectional area having a value in a range between about 0.17 mm$^2$ and 16.77 mm$^2$. In some embodiments, the through-holes 764 and 765 may have a cross-sectional area having a value in a range between about 0.1 mm$^2$ and 18 mm$^2$ to further restrict fluid flow to the pressure-sensing pathways 334 and 338 in order to further impede the inflow of fluids and exudates without inhibiting pressure sensing within the recessed space 744.

FIG. 10 is a perspective assembly view of the dressing interface 707. The top layer 731 and the base layer 732 of the dressing interface 707 may be covered with a top film coat 751 and a base film coat 752, respectively, which may be sealed around their perimeter by a weld to enclose the top layer 731 and the base layer 732. The top layer 731 and the top film coat 751 of the dressing interface 707 may each have ports 753 and 755, respectively, through which fluids from the fluid pathways 334, 336, and 338 may flow through the adapter 712 to the conduit 310. The dressing interface 707 may further comprise a fluid exit bond 757 which may be, for example, a weld between the top layer 731 and the top film coat 751 to seal their respective ports 753 and 755 to prevent leakage of fluids flowing through the ports 753 and 755. The base film coat 752 of the dressing interface 707 may have a port 743 concentric with the aperture 742 of the base layer 732. The dressing interface 707 may further comprise a fluid exit bond 759 which may be, for example, a weld between the base layer 732 and the base film coat 752 to seal the aperture 742 and the port 743 to prevent leakage of fluids flowing through them from the tissue interface 108 into the recessed space 744. The other side of the base film coat 752 may include an attachment device (not shown), such as the attachment device 142 described above with respect to FIG. 7. In some embodiments, a top drape 771 may be utilized to cover the applicator 708 of the dressing interface 707 to provide additional protection and support over the applicator 708 of the dressing interface 707 when the dressing interface 707 is applied to the tissue site. In some embodiments, the top drape 771 may also be utilized to cover any adhesive that might be exposed from applying the dressing interface 707 to the tissue site. In some embodiments, the top drape 771 may be similar to the cover 106 described above and, as such, may be a polymer such as a polyurethane film. In some embodiments, the dressing interface 707 including both the applicator 708 and the bridge 709 may have a length the ranges between about 15 cm to about 30 cm. In some embodiments, the applicator 708 the bridge 709 may be formed as a single device as shown. In other embodiments, the applicator 708 and the bridge 709 may be separate components that are coupled together to form a single device. In yet other embodiments, the applicator 708 and the bridge 709 may be separate components that may be used independently of each other as a single component in the therapy system 100.

Figure 12A:
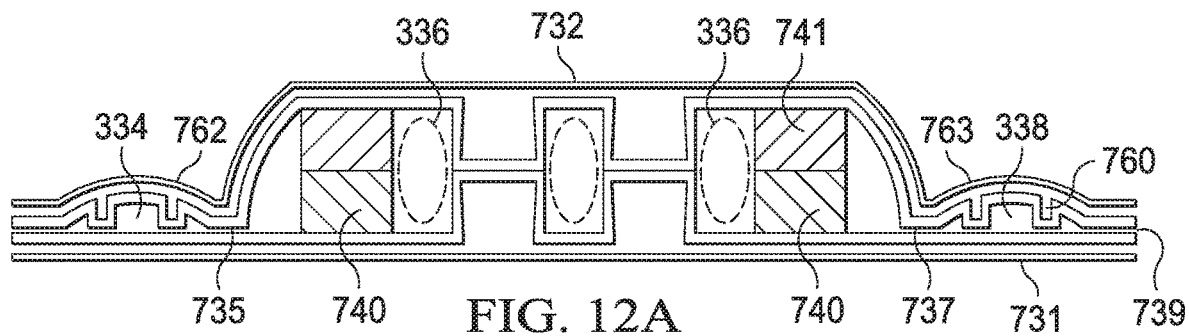
FIGS. 12A and 12B are cross-sectional views taken along lines 12A-12A and 12B-12B in FIG. 12 of the first embodiment of the bridge.
Figure 12B:
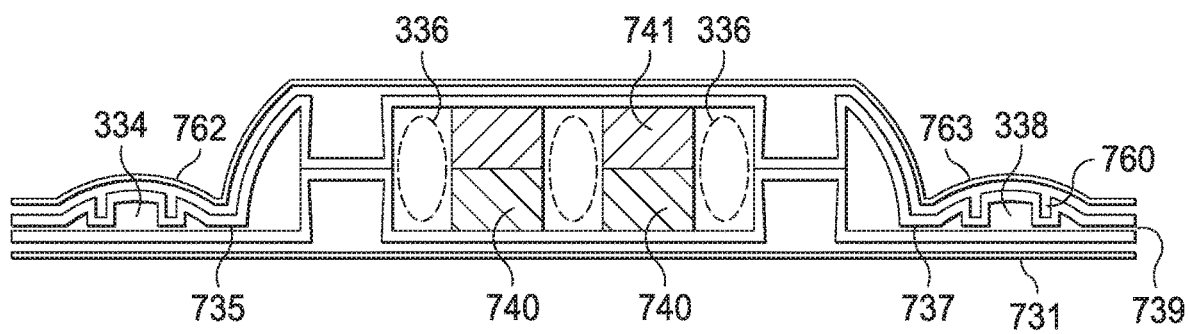

Referring to FIG. 12 is a plan view of a first embodiment of a bridge of the dressing interface 707 of FIG. 10, i.e., the bridge 709, for coupling the applicator 708 and the adapter 712 shown in FIGS. 11A and 11B, respectively. As indicated above, the closed cells 340 of the dressing interface 307 and the closed cells 640 of the dressing interface 607 may have a variety of shapes sized and arranged in different patterns within the sealed space, and the dressing interface 707 may have closed cells with some similarities to both. For example, the bridge 709 of the dressing interface 707 may comprise two sets of closed cells 740 and 741 having a generally cylindrical shape, one set of closed cells 740 extending from the top layer 731 and the other set of closed cells 741 extending from the base layer 732. In some embodiments, the two sets of closed cells 740 and 741 may be opposingly aligned so that the upper portion of the closed cells 740 extending from the top layer 731 face, or are aligned with, the upper portion of the closed cells 741 extending from the base layer 732. In some embodiments, the bridge 709 may include four rows of closed cells 740 and 741 wherein the closed cells 740 and 741 forming the two outside rows are offset or staggered from the closed cells 740 and 741 forming the two inside rows as shown. In this particular embodiment, the four rows of closed cells 740 and 741 form the negative pressure pathways 336 as indicated by the three arrows in FIG. 12 and the dashed line ovals shown in FIGS. 12A and 12B. Each of the walls 735 and 737 cooperate with the flange 739 to form the two fluid conductors 762 and 763 as described above. In some embodiments, the fluid conductors 762 and 763 may include standoffs or closed cells 760 to form the pressure sensing pathways 334 and 338 as shown in FIGS. 12A and 12B.

As can be seen, the closed cells 740 and 741 disposed in the negative pressure pathway 336 have a larger diameter and pitch than the smaller closed cells 760 that may increase fluid flow of negative pressure being applied to the tissue interface 108 to facilitate the removal of fluids and exudates within the recessed space 744. The closed cells 760 disposed in the pressure sensing pathways 334 and 338 have a noticeably smaller diameter and pitch than the larger closed cells 740 and 741 that may restrict fluid flow to facilitate pressure sensing within the recessed space 344 while impeding the inflow of fluids and exudates into the pressure sensing pathway 334. It should be understood that the arrangement and dimensions of the closed cells may be tailored to manage the delivery of negative pressure to the tissue interface 108 and the measurement of pressure within the recessed space 744 as described above with respect to the other embodiments.

In some embodiments, the bridges 709 may include closed cells 740 and 741 that are arranged in a different pattern depending upon the pneumatic requirements of the fluid pathways. FIG. 13, for example, is a plan view of a second embodiment of a bridge of the dressing interface 707, i.e., a bridge 809 for coupling the applicator 708 and the adapter 712 shown in FIGS. 11A and 11B, respectively.

Figure 13A:
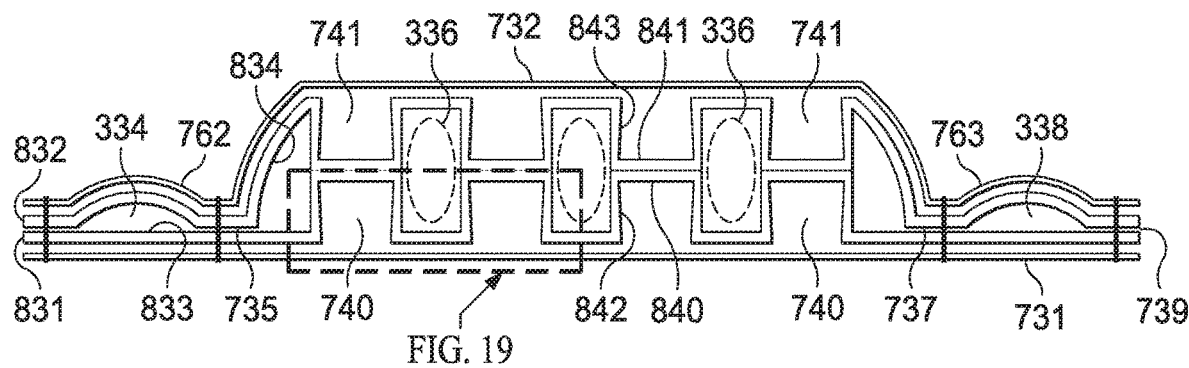
FIGS. 13A and 13B are cross-sectional views taken along lines 13A-13A and 13B-13B in FIG. 13 of the second embodiment of the bridge.
Figure 13B:
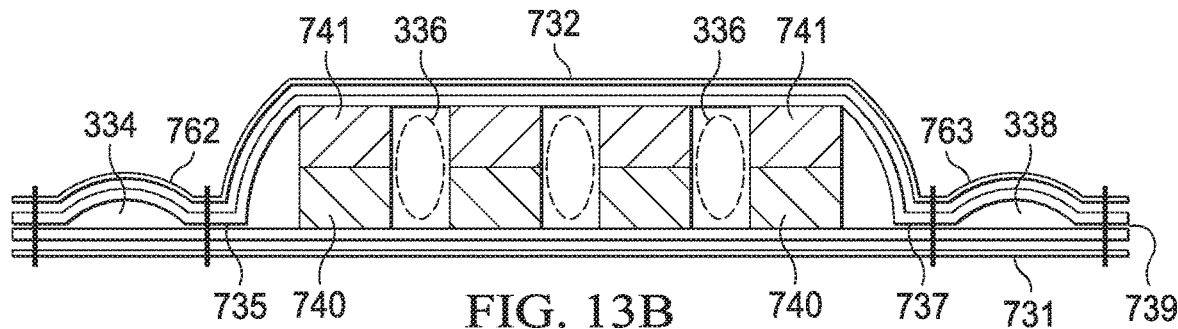

FIGS. 13, 13A and 13B are cross-sectional views taken along lines 13A-13A and 13B-13B in FIG. 13 of the bridge 809. The bridge 809 also includes four rows of closed cells 740 and 741, but in this embodiment the four rows are aligned both horizontally and vertically rather than being offset or staggered with each other. In some embodiments, the fluid conductors 762 and 763 may be opened and supported by a thicker base layer 732 as shown in FIG. 13. In still other embodiments, the fluid conductors 762 and 763 may comprise or be formed by tubes fluidly coupled to the pressure sensing pathways 344 and 338 in the bridge 709. As described above with respect to the other embodiments, the applicator 708 and the bridge 709 may have closed cells with different shapes arranged in different patterns that may be selected as the one best suited for the particular tissue site and the pneumatic requirements of negative pressure delivery and pressure sensing. For example, the applicator 708 of the dressing interface 707 also comprises the closed cells 740 that are arranged in a generally circular pattern within the recessed space 744 rather than the arrangement of rows in the bridge 709. The closed cells in the sealed space of the applicator 708 outside the recessed space 744 may also have different shapes arranged in a different pattern to accommodate the sensing pathways 334 and 338.

Figure 14:
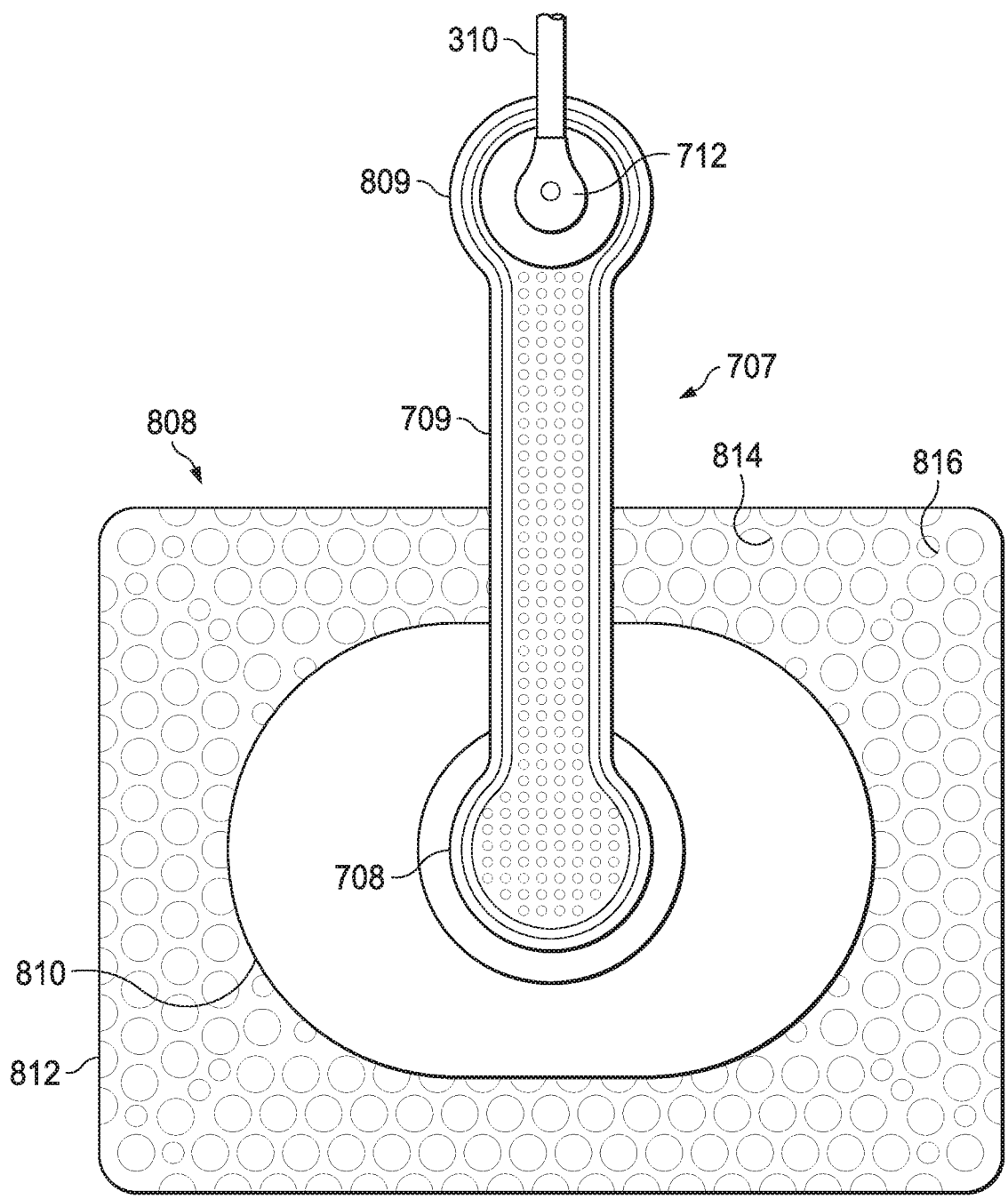
FIG. 14 is a plan view of a second embodiment of a bridge of the third dressing interface of FIG. 10, i.e., the bridge coupling the applicator and the adapter portion shown in FIGS. 11A and 11B, respectively.

In another example embodiment, the end of the bridge 709 and the adapter 712 may be fluidly coupled to an open space (not shown) within the adapter 712 as described above. Referring to FIG. 14, the end of the bridge 709 may further comprise a bulbous portion in some embodiments having a structure substantially similar to the structure of the applicator 708 described above such as, for example, a fluid coupler 809. The fluid coupler 809 also may comprise a recessed space (not shown) similar to the recessed space 744 that may be in fluid communication with the open space of the adapter 712. For example, the negative pressure pathway 336 may be fluidly coupled to the central lumen 328 through the recessed space of the fluid coupler 809 and the open space in the adapter 712 so that the negative pressure pathway 336 receives negative pressure from the negative pressure source 104 and delivers the negative pressure to the tissue interface 108 through the applicator 708. Correspondingly, pressure sensing pathways similar to the pressure sensing pathways 334 and 338 may be fluidly coupled to the peripheral lumens 322 of the conduit 310 so that the pressure sensing pathways are fluidly coupled to the pressure sensor 120 and in fluid communication with the recessed space 744 to sense negative pressure at the tissue interface 108. Each of the pressure sensing pathways may be fluidly coupled directly or indirectly to the peripheral lumens 322.

The dressing interface 707 with or without the fluid coupler 809 may be fluidly coupled to the tissue interface 108 as described above that in some embodiments may be the manifold 140 that is fluidly coupled to the recessed space 344 of the dressing interface 307 as shown in FIG. 7. As indicated above, the tissue interface 108 may comprise a variety of different dressings for negative pressure therapy. Still referring to FIG. 14, for example, a dressing 808 for treating tissue may be a composite of dressing layers, including a foam layer 810, a perforated silicone gel 812 having apertures 814 and 816, a fenestrated polyethylene film (not shown) disposed between the foam layer 810 and the perforated silicone gel 812, and an adhesive drape (not shown) covering all three layers. The fenestration pattern of the polyethylene film can be made in registration with the perforation pattern of at least a central area (not shown) of the silicone gel 812. In some embodiments, each of the perforations in the central area may have a width or diameter of about 2 millimeters, and each of the fenestrations in the polyethylene film may be slots having a length of about 3 millimeters and a width of about 0.5 millimeters to about 1 millimeter. The foam layer 810 may be foam having an open-cell structure, such as a reticulated foam. The foam may also be relatively thin and hydrophobic to reduce the fluid hold capacity of the dressing, which can encourage exudate and other fluid to pass quickly to external storage. The foam layer may also be thin to reduce the dressing profile and increase flexibility, which can enable it to conform to wound beds and other tissue sites under negative pressure. The adhesive drape may have an aperture or opening adapted to be fluidly coupled to the recessed space 744 of the applicator 708. Because of the size of the aperture 742 of the recessed space 744 as described above, alignment of the aperture 742 with the aperture of the adhesive drape when positioning the applicator 708 on the dressing 808 does not need to be as precise making it much easier to apply the tissue interface at the tissue site.

The fluid restrictions may comprise a plurality of linear slits or slots in some embodiments. For example, the fluid restrictions may comprise a plurality of linear slots having a length of approximately 4 millimeters or less, and a width of approximately 2 millimeters or less. A length of approximately 3 millimeters and a width of approximately 1 millimeter may be suitable for many therapeutic applications. In some embodiments, the fluid restrictions may be distributed across the polymer film in a uniform pattern, such as a grid of parallel rows and columns. In some embodiments, the fluid restrictions may be distributed across the polymer film in parallel rows and columns, and the rows may be spaced about 3 millimeters apart from each other. The fluid restrictions in each of the rows may also be spaced about 3 millimeters apart from each other in some examples.

Figure 15:
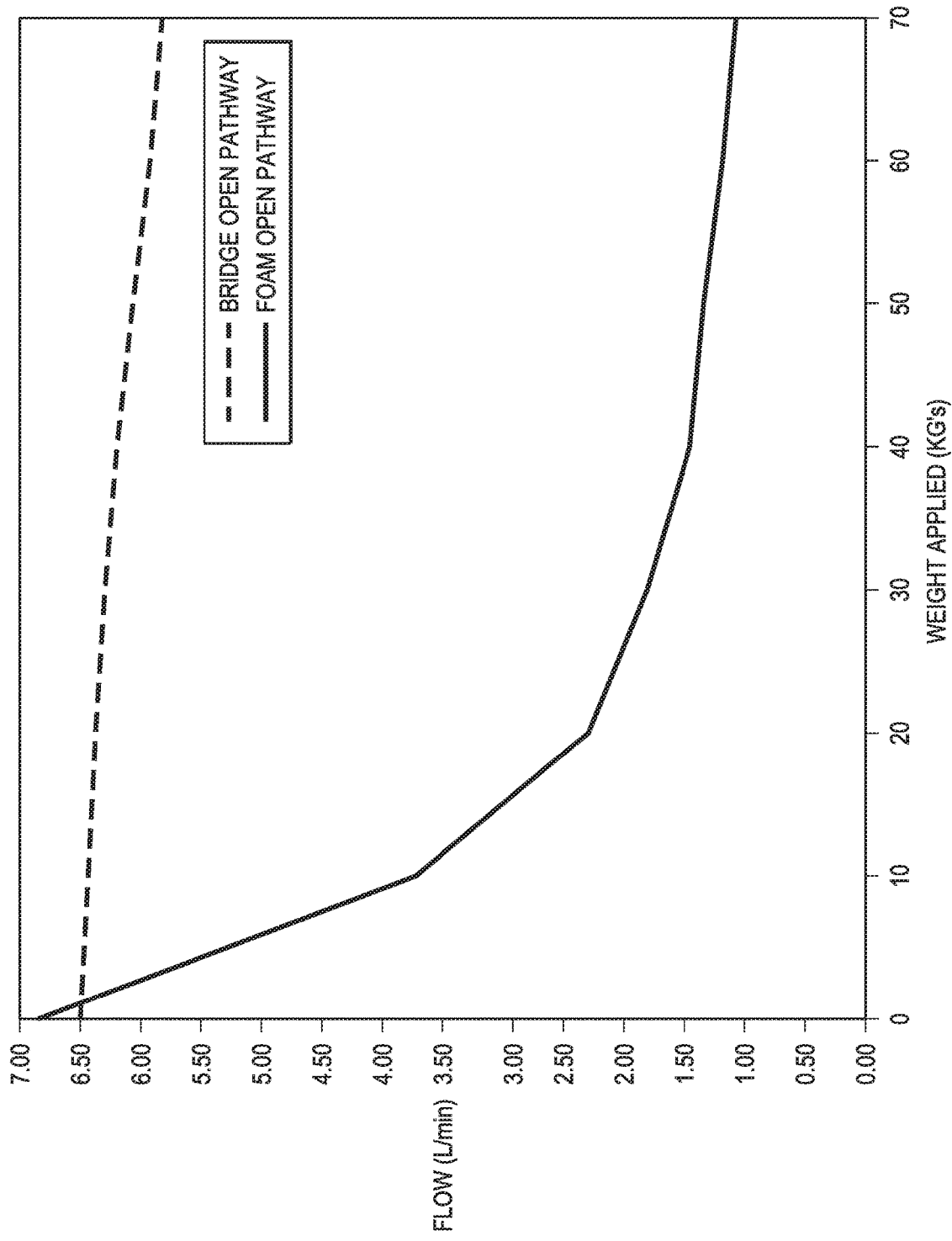
FIG. 15 is a graph illustrating flow rates (L/min) of fluids drawn through the third dressing interface of FIG. 10 that vary as a result of the application of a flat compressive force to the bridge of the third dressing interface.

FIG. 15 shows a first graph illustrating flow rates (L/min) of fluids drawn through the bridge 709 of the dressing interface 707 as shown by the dashed line that varies as a result of the application of a flat compressive force to the bridge 709 of the dressing interface 707. FIG. 15 shows a second graph illustrating flow rates (L/min) of fluids drawn through a foam conduit fluidly coupled to a standard elbow connector as shown by the solid line that also varies as a result of the application of a flat compressive force to the conduit portion of the elbow connector. In each case, 25 mmHg of negative pressure was applied by both the dressing interface 707 and the elbow connector to a foam pad with 1.0 mpas of fluid. Both devices were subjected to these compressive forces over a range of 0-70 kg. Fluid flow for the bridge 709 of the dressing interface 707 suffered a loss in fluid flow of only 10% at 70 kg, while the foam conduit suffered a loss of about 85% at 70 kg. Fundamentally, the flow rate through the bridge 709 of the dressing interface 707 exceeded the flow rate of the foam conduit over the entire range of 0-70 kg and, as such, is less susceptible to blockages. Thus, the performance of the bridge 709 of the dressing interface 707 exceeded the performance of the foam conduit with the application of flat a compressive force.

Figure 16:
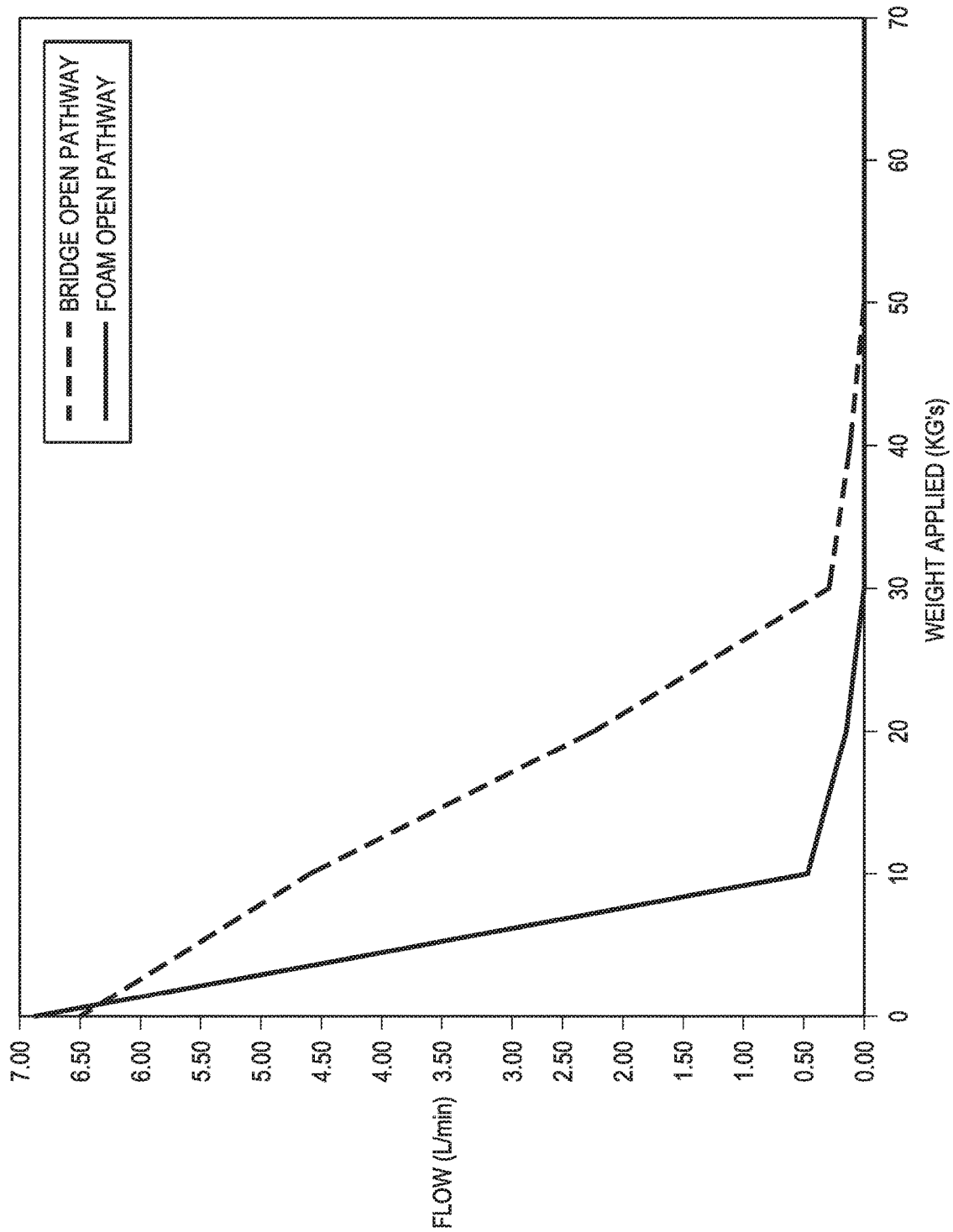
FIG. 16 is a graph illustrating flow rates (L/min) of fluids drawn through the third dressing interface of FIG. 10 that vary as a result of the application of a compressive force on a horizontal point of the bridge of the third dressing interface.

FIG. 16 shows a first graph illustrating flow rates (L/min) of fluids drawn through the bridge 709 of the dressing interface 707 as shown by the dashed line that varies as a result of the application of a compressive force on a horizontal point of the bridge 709 of the dressing interface 707 as opposed to a flat compressive force. FIG. 16 also shows a second graph illustrating flow rates (L/min) of fluids drawn through a foam conduit fluidly coupled to a standard elbow connector as shown by the solid line that also varies as a result of the application of a compressive force on a horizontal point of the conduit portion of the elbow connector. In each case, 25 mmHg of negative pressure was applied by both the dressing interface 707 and the elbow connector to a foam pad with 1.0 mpas of fluid. Both devices were subjected to these compressive forces over a range of 0-70 kg. The bridge 709 of the dressing interface 707 was able to maintain open flow when subjected to a compressive load of more than 10 to 20 kg greater than was subjected to the foam conduit. Thus, the performance of the bridge 709 of the dressing interface 707 exceeded the performance of the foam conduit with the application of a compressive force at a specific horizontal point because the bridge 709 is less susceptible to blockages.

Figure 17:
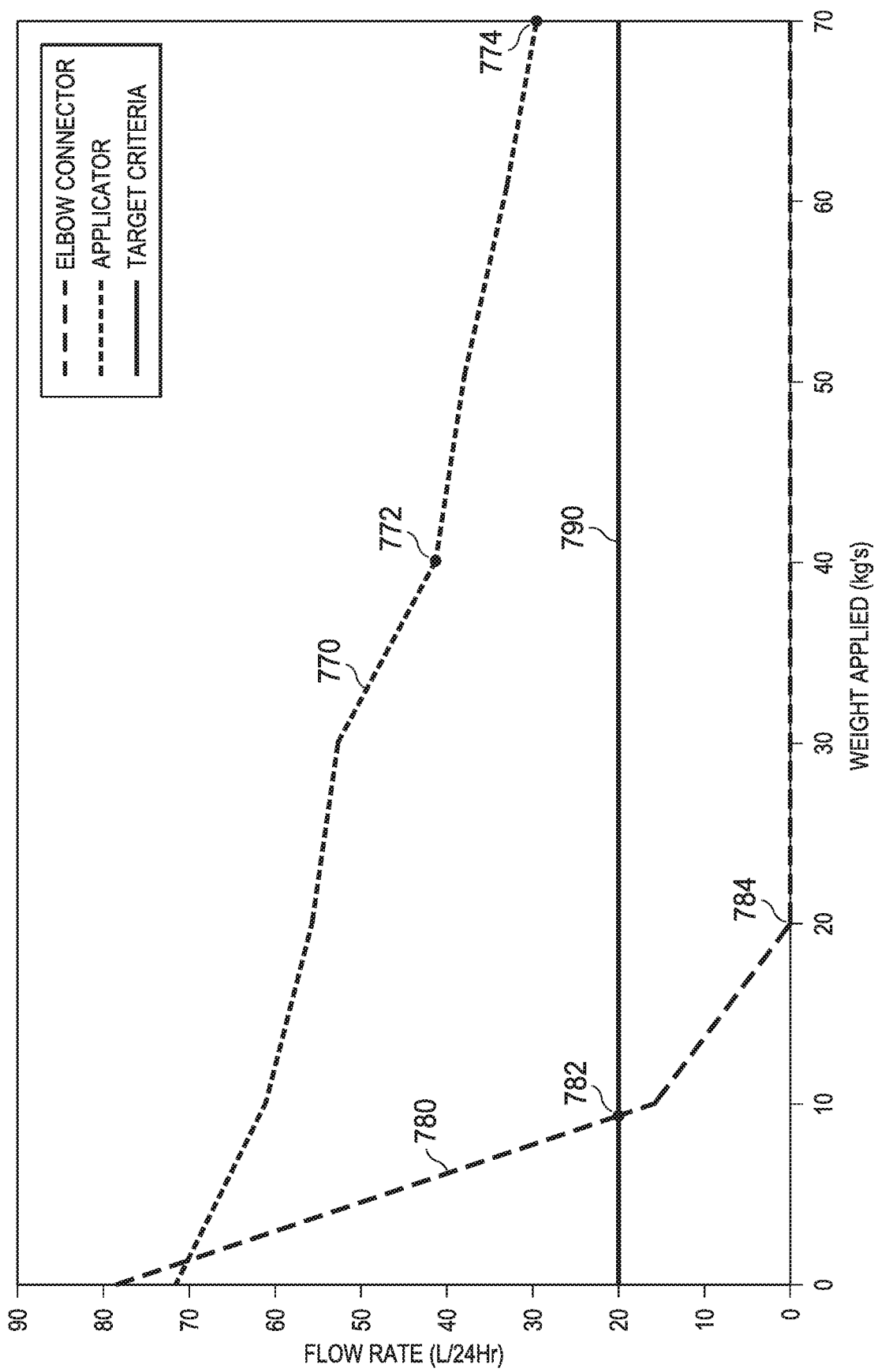
FIG. 17 is a graph illustrating flow rates of fluids drawn through the third dressing interface of FIG. 10 that vary as a result of the application of a compressive force to the applicator of the third dressing interface.

FIG. 17 shows a first graph illustrating flow rates (L/24 Hrs) of fluids drawn through the dressing interface 707 as shown by the dashed line 770 that vary as a result of the application of a compressive force to the applicator 708 of the dressing interface 707. FIG. 17 also shows a second graph illustrating flow rates (L/24 Hrs) of fluids drawn through a standard elbow connector and a conduit fluidly coupled to the connector as shown by the dashed line 780 that also vary as a result of the application of a compressive force to the elbow connector. In each case, 25 mmHg of negative pressure was applied by both the dressing interface 707 and the elbow connector to a foam pad with 1.0 mpas of fluid. The results for both devices were compared to a target criteria as shown by the solid line 790 that was set at a minimum value of 20 L/24 hrs over range of 0-70 kg for this type of tissue interface. Fluid flow for the dressing interface 707 was more than twice (100% above) the target criteria with the application of a compressive force of about 40 kg at 772, and still more than 33% above the target criteria at a maximum compressive force of 70 kg at 774. Fundamentally, the flow rate through the applicator 708 of the dressing interface 707 exceeds the minimum flow rate of 20 L/24 hrs over the entire range of 0-70 kg. In comparison, fluid flow for the standard elbow connector fell below the target criteria with the application of a compressive force of only 10 kg at 782, and fell to a zero flow rate or total blockage at a compression force of 20 kg at 784. The flow rate through the elbow connector not only did not exceed the minimum flow rate through the entire range of 0-70 kg, but also dropped quickly below the minimum flow rate at only 10 kg. Thus, the performance of the applicator 708 of the dressing interface 707 well exceeded the performance of the elbow portion of the elbow connector with the application of a compressive force.

Figure 18:
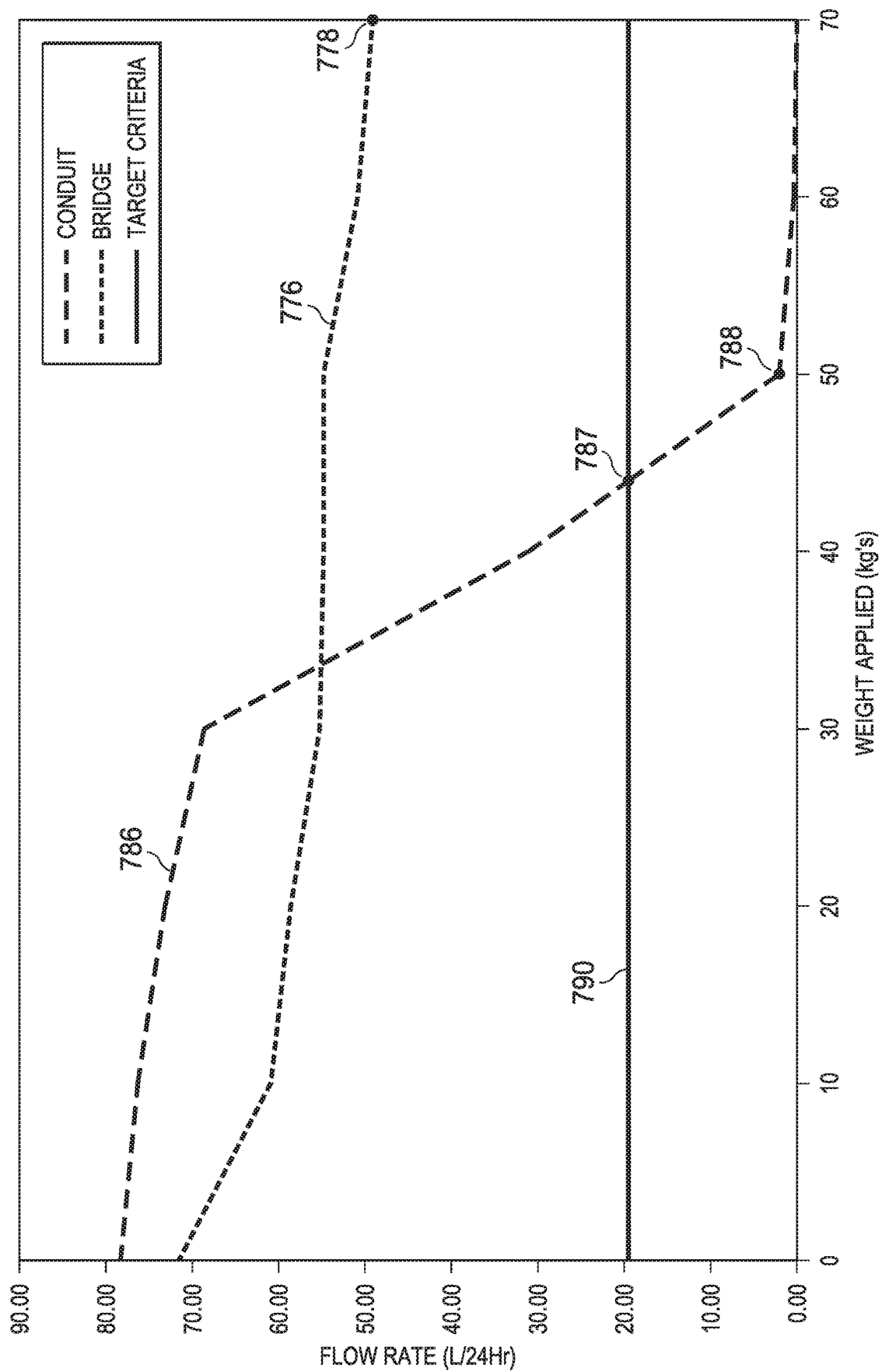
FIG. 18 is a graph illustrating the flow rates of fluids drawn through the third dressing interface of FIG. 10 that vary as a result of the application of a compressive force to the bridges of the third dressing interface.

FIG. 18 shows a first graph illustrating flow rates (L/24 Hrs) of fluids drawn through the dressing interface 707 as shown by the dashed line 776 that varies as a result of the application of a compressive force to the bridge 709 of the dressing interface 707. FIG. 18 also shows a second graph illustrating flow rates (L/24 Hrs) of fluids drawn through a standard elbow connector and a conduit fluidly coupled to the connector as shown by the dashed line 786 that also varies as a result of the application of a compressive force to the conduit portion of the elbow connector. In each case, 25 mmHg of negative pressure was applied by both the dressing interface 707 and the elbow connector to a foam pad with 1.0 mpas of fluid. The results for both devices were compared to the target criteria as shown by the solid line 790 that again was set at a minimum value of 20 L/24 hrs over range of 0-70 kg for this type of tissue interface. Fluid flow for the dressing interface 707 was about 150% above the target criteria with the application of a compressive force above the target criteria at a maximum compressive force of 70 kg at 778 on the bridge 709 of the dressing interface 707. Fundamentally, the flow rate through the bridge 709 of the dressing interface 707 exceeds the minimum flow rate of 20 L/24 hrs over the entire range of 0-70 kg. In comparison, fluid flow for the standard elbow connector fell below the target criteria with the application of a compressive force on the conduit portion of the elbow connector of only 45 kg at 787, and fell to a nearly zero flow rate or total blockage at a compression force of 50 kg at 788. The flow rate through the elbow connector not only did not exceed the minimum flow rate through the entire range of 0-70 kg, but also dropped quickly below the minimum flow rate at 45 kg. Thus, the performance of the bridge 709 of the dressing interface 707 exceeded the performance of the conduit portion of the elbow connector with the application of a compressive force.

As described above, the cellular structure of the dressing interface 707 including the bridge 709 and the applicator 708 may provide significant advantages of being able to sustain flow through the fluid pathways 334, 336 and 338 when subjected to compressive forces and the application of negative pressure. This may also be true for the cellular structures of the dressing interface 307 which may comprise a cellular structure having only closed cells 340 extending from the first layer 331 or another cellular structure having both closed cells 340 and closed cells 350 extending from the second layer 332. Regardless of the cellular structure, both of the dressing interface 307 and the dressing interface 707 may be used on wounds in pressure sensitive areas of the body such as, for example, a sacral wound, an area where the patient leans on or sits on while resting. Either one of the dressing interfaces may cause maceration to the tissue surrounding the wound, i.e., the periwound skin, causing pain and discomfort for the patient. Although the application of negative pressure to the wound by either the applicator 308 or the applicator 708 may remove most of the fluids and wound exudates from the tissue site, the second layer 332 and base layer 732 may comprise a relatively thick polymeric film having a relatively high MVTR.

For example, the dressing interface 707 comprises four layers of thick polymeric film including the top layer 731 and the base layer 732, also referred to collectively as outer layers 731 and 732, and the sheet material from which the closed cells 740 and 741 are formed, i.e., top sheet 831 and base sheet 832 referred to collectively as inner layers 831 and 832. These layers may each comprise a relatively thick polymeric film such as, for example, a thermoplastic polyurethane (TPU) film that is permeable to water vapor but impermeable to liquid. The outer layers 731 and 732 and the inner layers 831 and 832 may be breathable in various respects and may have MVTRs that are proportional to their thickness. For example, the MVTR may be at least 300 g/m$^2$ per twenty-four hours in some embodiments. In some embodiments, the combination of all four layers may reduce the MVTR to an unacceptable value. Thus, it may be desirable to provide the mechanical properties of a stack of film layers that has a relatively low natural MVTR (i.e., less than about 250 g/m$^2$) but establish a method to increase the breathability of the device itself and potentially limit the adverse effects of periwound maceration. Increasing the breathability of the device itself, e.g., the breathability of the dressing interface 707, would be desirable if the modification did not diminish the structural and low profile benefits associated with maintaining the flow of fluids through the fluid pathways 334, 336 and 338 when subjected to compressive forces and the application of negative pressure. In some example embodiments, managing moisture levels on the periwound skin may be accomplished by thinning the walls of the closed cells 740 and 741 with respect to the thickness of the inner layers 831 and 832. More specifically, managing moisture levels may be achieved by thinning the top portion or distal ends of the closed cells 740 and 741 while maintaining the thickness of the sidewalls of the closed cells 740 and 741 extending from the inner layers 831 and 832. So rather than having a stack of three or four layers, a dressing interface having closed cells with top portions that are thinned relative to the thickness of the individual layers would have a more favorable MVTR over the surface area defined by the footprint of the closed cells. For example, the footprint of the closed cells may be determined by the cell coverage percentage described above.

Figure 19:
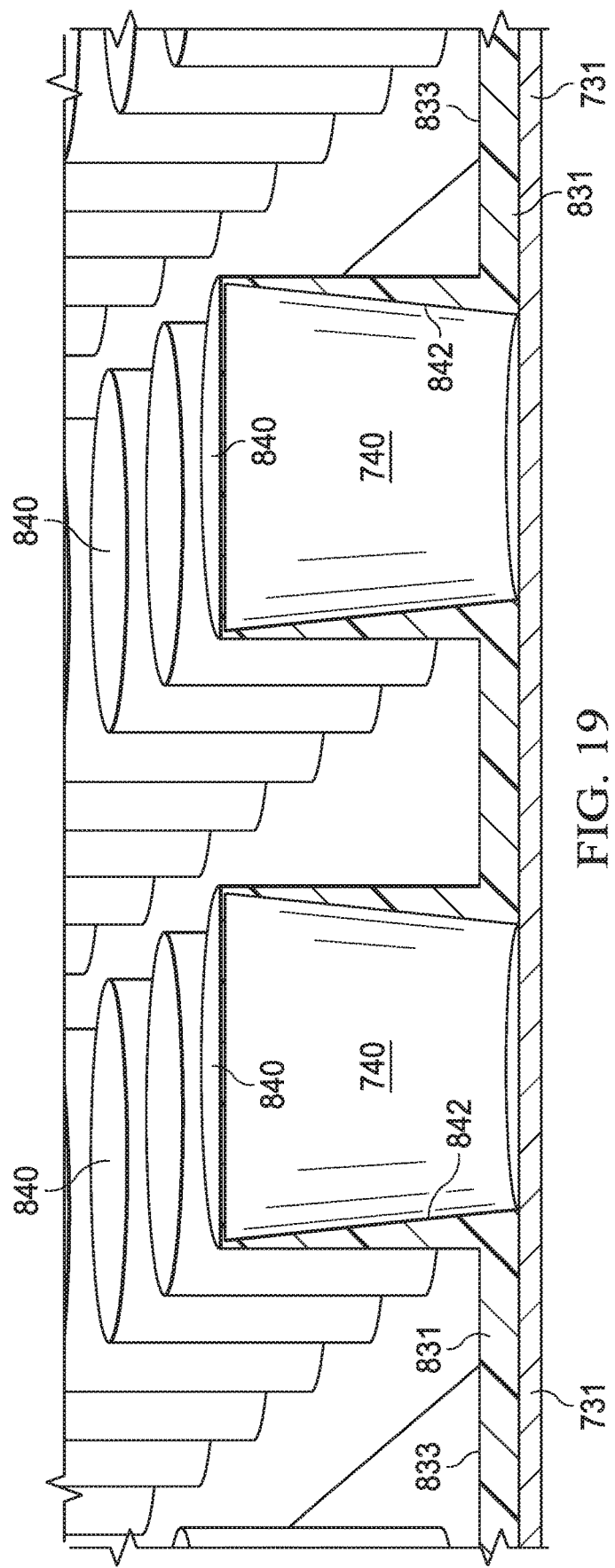
FIG. 19 is an exploded, perspective view of two rows of the closed cells of a section of the second embodiment of the bridge shown in FIG. 13A.

Referring to FIG. 19, an exploded, perspective view of a section of FIG. 13A is shown including two rows of the closed cells 740. In some example embodiments, the closed cells 740 and the closed cells 741 (not shown) may each be formed from the inner layers 831 and 832 (not shown) which may be a polymeric film with properties similar to those described above. In some embodiments, the closed cells 740 and the closed cells 741 may be formed from the inner layers 831 and 832 to comprise sidewalls tapering from to a distal surface. For example, a vacuum process may be used that draws the top sheet 831 into a tool or mold that forms the closed cells 740 with sidewalls 842 tapering from a surface 833 of the top sheet 831 to distal ends 840. Correspondingly, the vacuum process may be used to draw the bottom sheet 832 into a tool or mold that forms the closed cells 741 with sidewalls 843 tapering from a surface 834 of the top sheet 832 to distal ends 841. In some embodiments, the distal surfaces of the closed cells 740 and the closed cells 741 may be opposingly aligned as shown in FIGS. 13A and 13B and contact each other when the dressing interface 707 is subjected to the application of negative pressure or compressive forces. (The same is true for the dressing interface 307, except that the closed cells 340 and 350 are aligned against the opposing second layer 332 and the first layer 331, respectively, rather than each other.) As a result, the distal ends 840 of the closed cells 740 are thinned out to a thickness less than the thickness of the top sheet 831 while the sidewalls 842 remain sufficiently thick to support the fluid pathways 334, 336 and 338 during the application compressive forces and/or the application of negative pressure. Correspondingly, the distal ends 841 of the closed cells 741 may also, or alternatively, be thinned out to a thickness less than the thickness of the bottom sheet 832 while the sidewalls 843 remain sufficiently thick to support the fluid pathways 334, 336 and 338 during the application compressive forces and/or the application of negative pressure.

In some embodiments, the closed cells 740 may be formed from a top sheet 831 having a thickness that varies between about 250 µm and about 1000 µm. In some other embodiments, the sidewalls 842 may have a thickness before thinning progresses that varies between about 200 µm and about 700 µm. In still other embodiments, the distal ends 840 may have a thickness that varies between about 25 µm and about 250 µm. For such embodiments, the closed cells 740 may have a thinning ratio, i.e., the ratio between the thickness of the distal ends 840 and the thickness of the top sheet 831, as small as about 10%. For example, the closed cells 740 may be formed from a top sheet 831 having a thickness of about 370 µm such that the sidewalls 842 have a thickness of about 230 µm and the distal ends 840 have a thickness of about 50 µm. For this example, the closed cells 740 have a thinning ratio of about 13.5%. In some embodiments, the closed cells 741 may be formed from a bottom sheet 832 having a thickness that varies between about 250 µm and about 1000 µm. In some other embodiments, the sidewalls 843 may have a thickness before thinning progresses that varies between about 200 µm and about 700 µm. In still other embodiments, the distal ends 841 may have a thickness that varies between about 25 µm and about 250 µm. For such embodiments, the closed cells 741 may have a thinning ratio, i.e., the ratio between the thickness of the distal ends 841 and the thickness of the bottom sheet 832, as small as about 10%. For example, the closed cells 741 may be formed from a bottom sheet 832 having a thickness of about 370 µm such that the sidewalls 843 have a thickness of about 230 µm and the distal ends 841 have a thickness of about 50 µm. For this example, the closed cells 741 have a thinning ratio of about 13.5%.

In some embodiments, the amount of thinning of the distal ends 840 may be controlled by adjusting the draw ratio as described above. For example, the closed cells 740 may have a height of about 2.0 mm that may be formed from a top sheet 831 having a thickness of about 400 µm with a draw ratio of about 5:1 may yield a thinning ratio of about 12.5%. In another example, a draw ratio of about 3:1 may yield a thinning ratio of about 10%. In other example embodiments, the thinning ratio may be increased by increasing the draw ratio, which may be achieved by increasing the cross-sectional area of the closed cells 740 and there distal ends 840 being thinned and/or increasing the height of the closed cells 740. In some embodiments, increasing the cell coverage percentage as defined above may also increase the composite thinning across the surface area of the top sheet 831 for the dressing interface 707. For example, the top sheet 831 may be a Platilon® thermoplastic polyurethane film available from Convestro LLC, such as Platilon U 4201 Y/AU. In some embodiments, using a draw ratio of about 2.75:1 and a cell coverage percentage of about 33% with a top sheet 831 comprising this Platilon film and having a thickness of about 500 µm, increased the MVTR from about 60 g/m$^2$ per 24 hours to about 400 g/m$^2$ per 24 hours posting an increase in breathability and moisture management of about 600%.

Figure 20B:
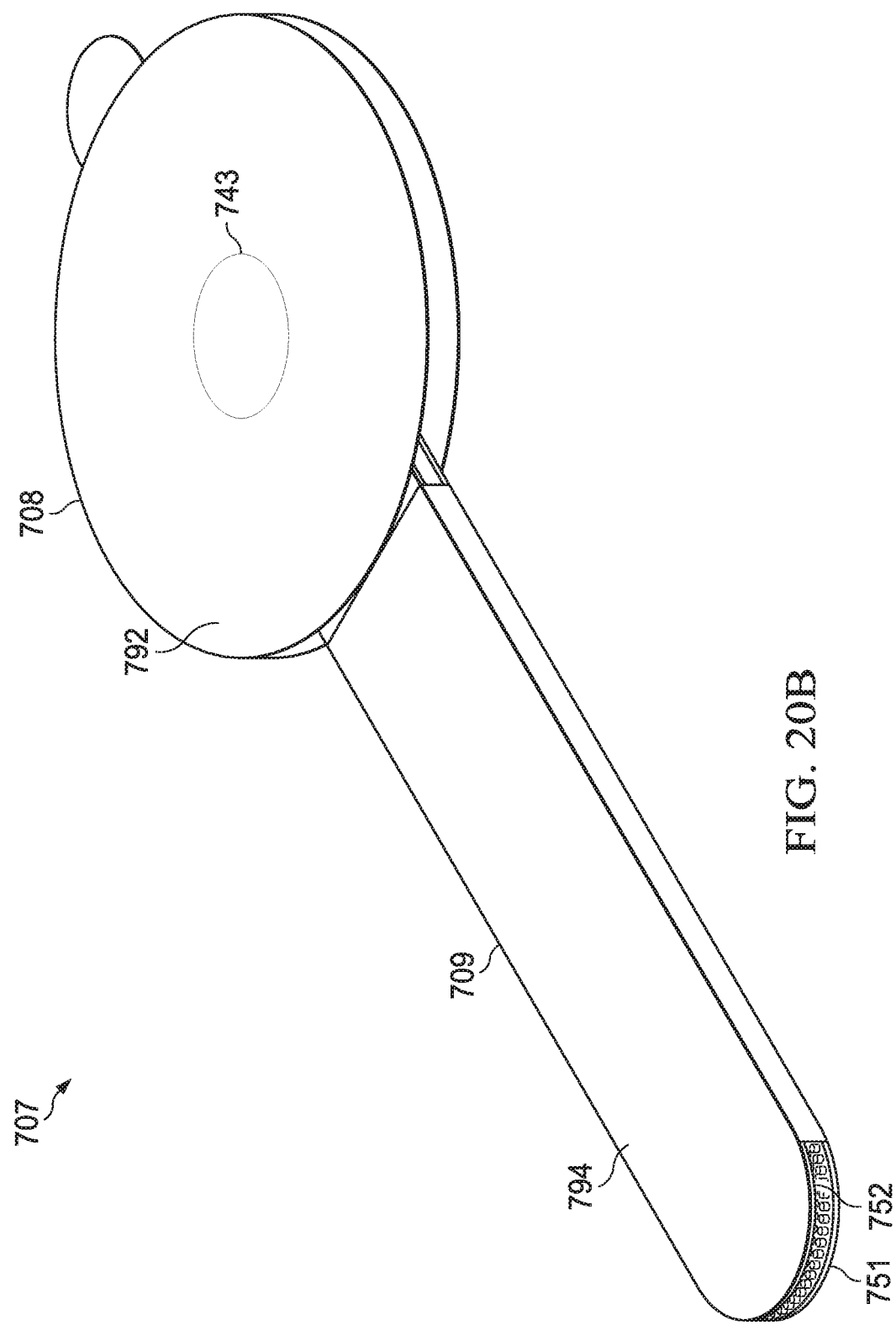

In some embodiments, the dressing interface 707 may further comprise a wicking system to further offload fluid from the periwound including material for evaporating fluids drawn from the periwound. Referring more specifically to FIGS. 20A and 20B, a top view and bottom view of the dressing interface 707 comprising the top layer 731 and the base layer 732 (see FIG. 10) that may be covered with the top film coat 751 and the base film coat 752, respectively. The top film coat 751 and the base film coat 752 may be sealed around their perimeter by a weld to enclose the top layer 731 and the base layer 732. In some example embodiments, the base film coat 752 may comprise a moisture offloading layer 794 that may be adapted to contact the tissue site for wicking fluids from the periwound. In some example embodiments, the top film coat 751 may comprise material for evaporating fluids drawn from the periwound such as, for example, moisture evaporation tabs 796 coupled to the top film coat 751. In some embodiments, the moisture evaporation tabs 796 may be fluidly coupled to the moisture offloading layer 794 to evaporate fluids offloaded from the moisture offloading layer 794 into the open air. In some embodiments, the moisture offloading layer 794 and the moisture evaporation tabs 796 may comprise the same materials used for both wicking and evaporation of fluids from the periwound. In yet other embodiments, the moisture offloading layer 794 and the moisture evaporation tabs 796 may be used independently for both wicking and evaporation of fluids from the periwound.

The moisture offloading layer 794 and the moisture evaporation tabs 796 may comprise a non-woven material such as, for example, a polyester non-woven material such as, for example, Libeltex TDL4. In some embodiments, other non-woven structures may be used such as, for example, Libeltex TDL2, or laminations with fiber or foam structures. Further, other materials may be used, such as a polyurethane film having a high MVTR that may provide for evaporation of condensate. In other embodiments, the moisture offloading layer 794 and the moisture evaporation tabs 796 may comprise materials that are hydrophilic in nature such as, for example, gels and foams that may be used to provide wicking and/or evaporation. For example, such materials may include one or more the following materials: hydrophilic polyurethane; cellulosics; hydrophilic polyamides; polyvinyl alcohol; polyvinyl pyrrolidone; hydrophilic acrylics; hydrophilic silicone elastomers; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; EVA film; co-polyester; silicones; a silicone drape; a 3M Tegaderm® drape; polyether block polyamide copolymer (PEBAX), for example, from Arkema, France; Expopack 2327; or other appropriate material.

A method for providing negative pressure to a sealed space in fluid communication with a tissue site is also disclosed. In one example embodiment, the method comprises positioning a tissue interface or manifold at a tissue site for delivering negative pressure to the tissue site, and coupling a recessed space of a dressing interface or a connector to the tissue interface or manifold wherein the dressing interface comprises a first fluid pathway and a second fluid pathway that are fluidly coupled to the recessed space in a side-by-side relationship. Such method further comprises applying negative pressure to the recessed space through the first fluid pathway formed by a first layer of polymeric film coupled to a second layer of polymeric film including features separating the first layer and the second layer to form the first pathway. Such method further comprises sensing the negative pressure within the recessed space through the second fluid pathway formed by the first layer and the second layer including features separating the first layer and the second layer to form the second pathway. The features or closed cells within the first pathway and the second pathway may prevent the pathways from collapsing as a result of apposition forces generated by the application of negative pressure to the dressing interface or connector. These features or closed cells may also prevent the negative pressure or pressure sensing from being blocked as a result of external forces being applied to the dressing interface or connector.

The systems, apparatuses, and methods described herein may provide other significant advantages. For example, some therapy systems include a closed system that does not provide airflow to a tissue interface frequently enough which may result in the creation of a significant head pressure. The head pressure in some embodiments may be defined as a difference in pressure (DP) between a negative pressure set by a user or caregiver for treatment, i.e., the target pressure (TP), and the negative pressure provided by a negative pressure source that is necessary to offset the pressure drop inherent in the fluid conductors, i.e., the supply pressure (SP), in order to achieve or reach the target pressure (TP). For example, the head pressure that a negative pressure source needs to overcome may be as much as 75 mmHg. Problems may occur in such closed systems when a blockage occurs in the pneumatic pathway of the fluid conductors that causes the negative pressure source to increase to a value above the normal supply pressure (SP) as a result of the blockage. For example, if the blockage suddenly clears, the instantaneous change in the pressure being supplied may cause harm to the tissue site. Consequently, the supply pressure (SP) is limited to a maximum value that cannot be exceeded in order to avoid the possibility of causing harm to the tissue site.

Some therapy systems have attempted to compensate for head pressure by introducing a supply of ambient air flow into the therapeutic environment by providing a vent on the dressing to provide ambient air flow into the therapeutic environment as a controlled leak. However, such a vent typically includes a filter that could become blocked when the dressing is applied or if the user or patient accidentally sits on the vent after the dressing is applied. Locating the filter in such a location may also be problematic because it is more likely to be contaminated or compromised by other chemicals and agents associated with treatment utilizing instillation fluids that could adversely affect the performance of the filter and the vent itself.

The embodiments of the therapy systems described above may overcome the problems associated with having a large head pressure in a closed pneumatic environment, and the problems associated with using a vent disposed on or adjacent the dressing. More specifically, the embodiments of the therapy systems described above may resolve such problems by fluidly coupling the therapeutic environment to a fluid regulator such as, for example, the regulator 118 in FIG. 1, through any one of the fluid pathways so that the fluid regulator is separated from the dressing 102. For example, either one of the pressure sensing pathways 334 or 338 may be used as a fluid conductor between the therapeutic space and the regulator. In embodiments of therapy systems that include an air flow regulator comprising a filter and a fluid conductor, the filter maintains a substantially constant airflow and provides a continuous flow of a mixture of wound fluids and ambient air into the canister as described above. Moreover, such embodiments reduce the head pressure associated with the fluid conductors of the therapeutic system so that the negative pressure source can achieve the same target pressure (TP) with a lower supply pressure (SP). Such therapy systems utilizing an air flow regulator as described above are not only safer, but also require less battery power to generate the same target pressure (TP). Such therapeutic systems including airflow regulators also facilitate detection of blockages in the fluid conductors because erroneous blockages will be less likely to be confused with the elimination of a systemic leak.

In embodiments of therapy systems that include an air flow regulator comprising a valve such as the solenoid valve described above, the valve provides a controlled airflow as opposed to a constant airflow. The valve of the air flow regulator otherwise possesses many similarities to the filter embodiment and the same benefits as described above. The controller may be programmed to periodically open the solenoid valve as described above allowing ambient air to flow into the fluid pathway and dressing interface for a predetermined duration of time and consequently providing a predetermined volume of airflow into the pneumatic system. This feature allows the controller to activate the solenoid valve in a predetermined fashion to purge any blockages that may develop in the fluid pathways or the recessed space during operation. In some embodiments, the controller may be programmed to open the solenoid valve for a fixed period of time at predetermined intervals such as, for example, for five seconds every four minutes to mitigate the formation of any blockages.

In some other embodiments, the controller may be programmed to open the solenoid valve in response to a stimulus within the pneumatic system rather than, or additionally, being programmed to function on a predetermined therapy schedule. For example, if the pressure sensor is not detecting pressure decay in the canister, this may be indicative of a column of fluid forming in the fluid pathway or the presence of a blockage in the fluid pathway. Likewise, the controller may be programmed to recognize that an expected drop in canister pressure as a result of the valve opening may be an indication that the fluid pathway is open. The controller may be programmed to conduct such tests automatically and routinely during therapy so that the patient or caregiver can be forewarned of an impending blockage. The controller may also be programmed to detect a relation between the extent of the deviation in canister pressure resulting from the opening of the valve and the volume of fluid with in the fluid pathway. For example, if the pressure change within the canister is significant when measured, this could be an indication that there is a significant volume of fluid within the fluid pathway. However, if the pressure change within the canister is not significant, this could be an indication that the plenum volume was larger.

The systems, apparatuses, and methods described herein may provide other significant advantages. For example, when the first and second fluid conductors are combined into a single fluid conductor as described above, the single fluid conductor may simplify use of the system. Additionally, the single fluid conductor may be fluidly coupled directly to the canister allowing the user or caregiver to connect only one conductor to the therapy system rather than two separate fluid conductors.

Another advantage is that the disposable elements can be combined with the mechanical elements in a variety of different ways to provide therapy. For example, in some embodiments, the disposable and mechanical systems can be combined inline, externally mounted, or internally mounted. Additionally, the applicator the bridge of the dressing interfaces described above may be formed as separate components that are coupled together to form a single device. In yet other embodiments, the applicator and the bridge may be separate components that may be used independently of each other as a single component in the therapy system.

While shown in a few illustrative embodiments, a person having ordinary skill in the art will recognize that the systems, apparatuses, and methods described herein are susceptible to various changes and modifications. For example, certain features, elements, or aspects described in the context of one example embodiment may be omitted, substituted, or combined with features, elements, and aspects of other example embodiments. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

In some embodiments, the dressing interface may comprise a "top" layer and a "base" layer that are not limiting with respect to the orientation of the dressing interface. For example, the dressing interface 307 may comprise a top layer such as, for example, the first layer 331, and a base layer such as, for example, the second layer 332, coupled to the first layer 331 around the periphery of the first layer 331 to form a sealed space within the dressing interface 307. Thus, the sealed space may be formed between the first layer 331 and the second layer 332 of both the applicator 308 and the bridge 309 of the dressing interface 307.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for managing fluid in a system for treating a tissue site, the apparatus comprising:
    a first layer including polymeric film;
    a second layer including polymeric film coupled to the first layer to form a sealed space between the first layer and the second layer, the sealed space including a port at a proximal end of the sealed space;
    a first inner layer including a polymeric film disposed between the first layer and the second layer and defining a plurality of closed cells with the first layer, the closed cells including sidewalls having a thickness tapering from the first layer to a distal end of the closed cells within the sealed space; and
    an applicator having an aperture formed in the second layer at a distal end of the sealed space, wherein the aperture exposes a portion of the plurality of closed cells to define a recessed space adapted to be fluidly coupled to the tissue site.

2. The apparatus of claim 1, wherein the polymeric film is polyurethane having an average thickness between about 250 μm and about 1000 μm.

3. The apparatus of claim 1, wherein the polymeric film is polyurethane having an average thickness between about 250 μm and about 1000 μm and the distal end of the closed cells have an average thickness between about 50 μm and about 250 μm.

4. The apparatus of claim 1, wherein the polymeric film is polyurethane and the distal ends of the closed cells have a thickness of less than about 40% of a thickness of the first layer or the second layer.

5. The apparatus of claim 4, wherein the distal ends of the closed cells have a thickness greater than about 10% of a thickness of the first layer or the second layer.

6. The apparatus of claim 4, wherein the first inner layer including the distal ends of the closed cells together with the first layer have a MVTR greater than about 300 g/m$^2$ per 24 hours.

7. The apparatus of claim 4, wherein the first inner layer including the distal ends of the closed cells together with the second layer have a MVTR greater than about 300 g/m$^2$ per 24 hours.

8. The apparatus of claim 1, further comprising a first barrier coupled between the first layer and the second layer to form two fluid pathways within the sealed space extending between the recessed space and the port.

9. The apparatus of claim 8, further comprising a second barrier coupled between the first layer and the second layer to form a total of three fluid pathways within the sealed space extending between the recessed space and the port.

10. The apparatus of claim 9, wherein the three fluid pathways comprise a first fluid pathway formed between the first barrier and the second barrier, a second fluid pathway formed between the seal and the first barrier, and a third fluid pathway formed between the seal and the second barrier.

11. The apparatus of claim 10, wherein the port comprises a first port coupled to the first fluid pathway and adapted to be fluidly coupled to a source of negative pressure.

12. The apparatus of claim 11, wherein the port further comprises a second port coupled to the second fluid pathway and a third port coupled to the third fluid pathway, wherein both the second port and the third port are adapted to be fluidly coupled to a pressure sensor.

13. The apparatus of claim 1, wherein the second layer is adapted to contact the distal ends of the closed cells when negative pressure is applied to the port.

14. The apparatus of claim 1, further comprising a second inner layer including a polymeric film disposed between the first layer and the second layer and defining a plurality of closed cells with the second layer, the closed cells including sidewalls having a thickness tapering from the second layer to a distal end within the sealed space.

15. The apparatus of claim 14, wherein the polymeric film is polyurethane and the distal ends of the closed cells have a thickness between about 10% and about 40% of a thickness of either the first layer or the second layer.

16. The apparatus of claim 14, wherein the plurality of closed cells extending from the second layer and the first layer are arranged in rows that are staggered.

17. The apparatus of claim 14, wherein the plurality of closed cells extending from the second layer and the first layer are arranged in rows that are aligned.

18. The apparatus of claim 14, wherein the plurality of closed cells extending from the second layer are arranged to interleave with the plurality of closed cells extending from the first layer.

19. The apparatus of claim 14, wherein the polymeric film is polyurethane having an average thickness between about 250 µm and about 1000 µm and the distal ends of the closed cells have an average thickness between about 50 µm and about 250 µm.

20. The apparatus of claim 1, wherein the closed cells have a circular base having an average diameter between about 1 mm and about 10 mm.

21. The apparatus of claim 1, wherein the closed cells have an average height between about 2 mm and about 5 mm.

22. The apparatus of claim 1, wherein the closed cells have an average pitch between about 1 mm and about 10 mm between adjacent closed cells.

23. The apparatus of claim 1, wherein the polymeric film is any one taken from the group of high density polyethylene, low density polyethylene, and linear low density polyethylene, and polyurethane.

24. The apparatus of claim 1, wherein the polymeric film is polyurethane having a yield strength greater than about 10 MPa.

25. The apparatus of claim 1, wherein the polymeric film is polyurethane having an average thickness of about 400 µm and wherein the closed cells have a draw ratio ranging from about 5:1 to about 13:1.

26. The apparatus of claim 1, wherein the polymeric film is polyurethane having an average thickness of about 600 µm and wherein the closed cells have a draw ratio ranging from about 3:1 to about 9:1.

27. The apparatus of claim 1, wherein the closed cells have an internal pressure greater than the atmospheric pressure.

28. The apparatus of claim 1, wherein the closed cells have an internal pressure less than about 25 psi above the atmospheric pressure.

29. An apparatus for managing fluid in a system for treating a tissue site, the apparatus comprising:
    a first layer including a polymeric film;
    a second layer including a polymeric film coupled to the first layer with a seal forming a sealed space between the first layer and the second layer;
    a first inner layer including a polymeric film disposed between the first layer and the second layer and defining a plurality of closed cells with the first layer, the closed cells including sidewalls having a thickness tapering from the first layer to a distal end within the sealed space; and
    a second inner layer including a polymeric film disposed between the first layer and the second layer and defining a plurality of closed cells with the second layer, the closed cells including sidewalls having a thickness tapering from the second layer to a distal end of the closed cells within the sealed space.

30. The apparatus of claim 29, wherein the distal ends of the closed cells extending from the second layer are arranged to contact the distal ends of the closed cells extending from the first layer.

31. The apparatus of claim 29, wherein the polymeric film is polyurethane having an average thickness between about 250 µm and about 1000 µm and the distal ends of the closed cells have an average thickness between about 50 µm and about 250 µm.

32. The apparatus of claim 29, further comprising a barrier coupled between the first layer and the second layer to form two fluid pathways within the sealed space.

33. The apparatus of claim 29, wherein the sealed space is formed between the first inner layer and the second inner layer.

34. An apparatus for managing fluid in a system for treating a tissue site, the apparatus comprising:
    a top layer including a polymeric film having a plurality of closed cells including sidewalls tapering from the top layer to a distal end of the closed cells;
    a base layer including a polymeric film coupled to the top layer with a seal forming a sealed space between the top layer and the base layer, the base layer further including a plurality of closed cells having sidewalls tapering from the base layer to a distal end of the closed cells; and
    a barrier coupled between the top layer and the base layer to form two fluid pathways within the sealed space.

35. The apparatus of claim 34, wherein the distal ends of the closed cells extending from the top layer are arranged to contact the distal ends of the closed cells extending from the base layer.

36. The apparatus of claim 34, wherein the polymeric film is polyurethane having an average thickness between about 250 µm and about 1000 µm and the distal ends of the closed cells have an average thickness between about 50 µm and about 250 µm.

37. The apparatus of claim 34, wherein the top and the base layers including the distal ends of the closed cells together have a MVTR greater than about 300 g/m$^2$ per 24 hours.

38. The apparatus of claim 34, further comprising an applicator having an aperture formed in the base layer at the distal end of the sealed space, wherein the aperture exposes a portion of the plurality of closed cells to define a recessed space adapted to be fluidly coupled to the tissue site.

* * * * *